(12) United States Patent
Rieping et al.

(10) Patent No.: US 7,666,634 B2
(45) Date of Patent: *Feb. 23, 2010

(54) **FERMENTATION PROCESS FOR THE PREPARATION OF L-AMINO ACID USING MODIFIED *ESCHERICHIA COLI* WHEREIN THE YTFP-YJFA GENE REGION IS INACTIVATED**

(75) Inventors: Mechthild Rieping, Bielefeld (DE); Christine Bastuck, Bielefeld (DE); Thomas Hermann, Bielefeld (DE); Georg Thierbach, Bielefeld (DE)

(73) Assignee: Evonik Degussa GmbH, Essen (DE)

( * ) Notice: Subject to any disclaimer, the term of this patent is extended or adjusted under 35 U.S.C. 154(b) by 486 days.

This patent is subject to a terminal disclaimer.

(21) Appl. No.: 11/138,429

(22) Filed: May 27, 2005

(65) Prior Publication Data

US 2005/0221451 A1 Oct. 6, 2005

Related U.S. Application Data

(62) Division of application No. 09/963,668, filed on Sep. 27, 2001, now Pat. No. 6,916,637.

(60) Provisional application No. 60/237,610, filed on Apr. 10, 2000.

(30) Foreign Application Priority Data

| Sep. 30, 2000 | (DE) | ............... 100 48 605 |
| Nov. 9, 2000 | (DE) | ............... 100 55 516 |
| Jun. 22, 2001 | (DE) | ............... 101 30 192 |

(51) Int. Cl.
| *C12P 13/08* | (2006.01) |
| *C12P 13/06* | (2006.01) |
| *C12N 1/21* | (2006.01) |
| *C12N 15/00* | (2006.01) |
| *C12P 21/00* | (2006.01) |
| *C07K 14/00* | (2006.01) |
| *C07H 21/00* | (2006.01) |

(52) U.S. Cl. ............ 435/115; 435/116; 435/252.33; 435/69.1; 435/320.1; 530/350; 536/23.1

(58) Field of Classification Search ............ 435/115, 435/116, 252.33, 69.1, 320.1; 530/350; 536/23.1
See application file for complete search history.

(56) References Cited

FOREIGN PATENT DOCUMENTS

EP 1094111 A2 10/2000

OTHER PUBLICATIONS

Goldie et al., "Physical and Genetic Analysis . . .", Mol. Gen. Genet. 220(2):191-196, 1990.
Medina et al., "Sequence of the pck . . .", J. Bacteriol. 172(12):7151-7156, 1990.
Prost et al., "Detection of an extended . . .", Biochimie 81(3):197-200, 1999.
Kramer, "Genetic and physiological . . .", Journal of Biotechnology, vol. 45, No. 1, Feb. 12, 1996, pp. 1-21.
Rivolta, Carlo et al., "A 35.7 kb DNA fragment from the *Bacillus subtilis* chromosome containing a putative 12.3 kb operon involved in hexuronate catabolism and a perfectly symmectrical hypothetical catabolite-responsive element", Microbiology 144:877-884, 1998.
Blomfield et al., "Allelic exchange in *Escherichia-coli* using the *Bacillus-subtilis* sac-B gene and a temperature-sensitive psc-101 replicon", Dept. Microbiol. Immunol., Univ. Michigan Med. Sch., Molecular Microbiology, 5(6):1447-1457, 1991.
Hou et al., "A Mutant Phosphocnolpyruvate Carboxykinase in *Eseherichia coli* Conferring Oxaloacetate Decarboxylase Activity," Journal of Bacteriology, vol. 177 ( No. 6), p. 1620-23, ( Mar. 1995).

*Primary Examiner*—Delia M Ramirez
(74) *Attorney, Agent, or Firm*—Pillsbury Winthrop Shaw Pittman LLP

(57) ABSTRACT

The present invention relates to a fermentation process for the preparation of L-amino acids in which the following steps are carried out: (a) fermentation of the microorganisms of the family Enterobacteriaceae producing the desired L-amino acid, in which microorganisms' open reading frames of yjfA and ytfP are individually or jointly inactivated by one or more methods of mutagenesis selected from the group consisting of deletion, insertional mutagenesis due to homologous recombination, and transition or tranversion mutagenesis with incorporation of a non-sense mutation in the yjfA and ytfP gene region; (b) concentration of the fermentation broth to eliminate water and increase the concentration of said L-amino acids; and (c) isolation of the L-amino acids.

5 Claims, 5 Drawing Sheets

FERMENTATION PROCESS FOR THE PREPARATION OF L-AMINO ACID USING MODIFIED *ESCHERICHIA COLI* WHEREIN THE YTFP-YJFA GENE REGION IS INACTIVATED

CROSS REFERENCE TO RELATED APPLICATIONS

This is a divisional of U.S. patent application Ser. No. 09/963,668, filed Sep. 27, 2001, now U.S. Pat. No. 6,916,637, which claims priority to U.S. Provisional Patent Appl. No. 60/237,610, filed Oct. 4, 2000, and German Patent Application Nos. 100 48 605.3, 100 55 516, and 101 30 192.8, filed Sep. 30, 2000, Nov. 9, 2000, and Jun. 22, 2001, respectively.

FIELD OF THE INVENTION

The present invention relates to a fermentation process for the preparation of L-amino acids, especially L-threonine, using strains of the family Enterobacteriaceae in which at least the pckA gene is attenuated.

PRIOR ART

L-Amino acids are used in animal nutrition, in human medicine and in the pharmaceutical industry.

It is known to prepare L-amino acids by the fermentation of strains of Enterobacteriaceae, especially *Escherichia coli* and *Serratia marcescens*. Because of their great importance, attempts are constantly being made to improve the preparative processes. Improvements to the processes may relate to measures involving the fermentation technology, e.g. stirring and oxygen supply, or the composition of the nutrient media, e.g. the sugar concentration during fermentation, or the work-up to the product form, e.g. by ion exchange chromatography, or the intrinsic productivity characteristics of the microorganism itself.

The productivity characteristics of these microorganisms are improved by using methods of mutagenesis, selection and mutant choice to give strains which are resistant to antimetabolites, e.g. the threonine analogue α-amino-β-hydroxyvaleric acid (AHV) or auxotrophic for metabolites of regulatory significance, and produce L-amino acids, e.g. L-threonine.

Methods of recombinant DNA technology have also been used for some years to improve L-amino acid-producing strains of the family Enterobacteriaceae by amplifying individual amino acid biosynthesis genes and studying the effect on production.

OBJECT OF THE INVENTION

The object which the inventors set themselves was to provide novel procedures for improving the preparation of L-amino acids, especially L-threonine, by fermentation.

SUMMARY OF THE INVENTION

The invention provides a fermentation process for the preparation of L-amino acids, especially L-threonine, using microorganisms of the family Enterobacteriaceae which, in particular, already produce L-threonine and in which the nucleotide sequence (pckA gene) coding for the enzyme phosphoenolpyruvate carboxykinase (PEP carboxykinase) (EC 4.1.1.49) is attenuated.

Figure 1:
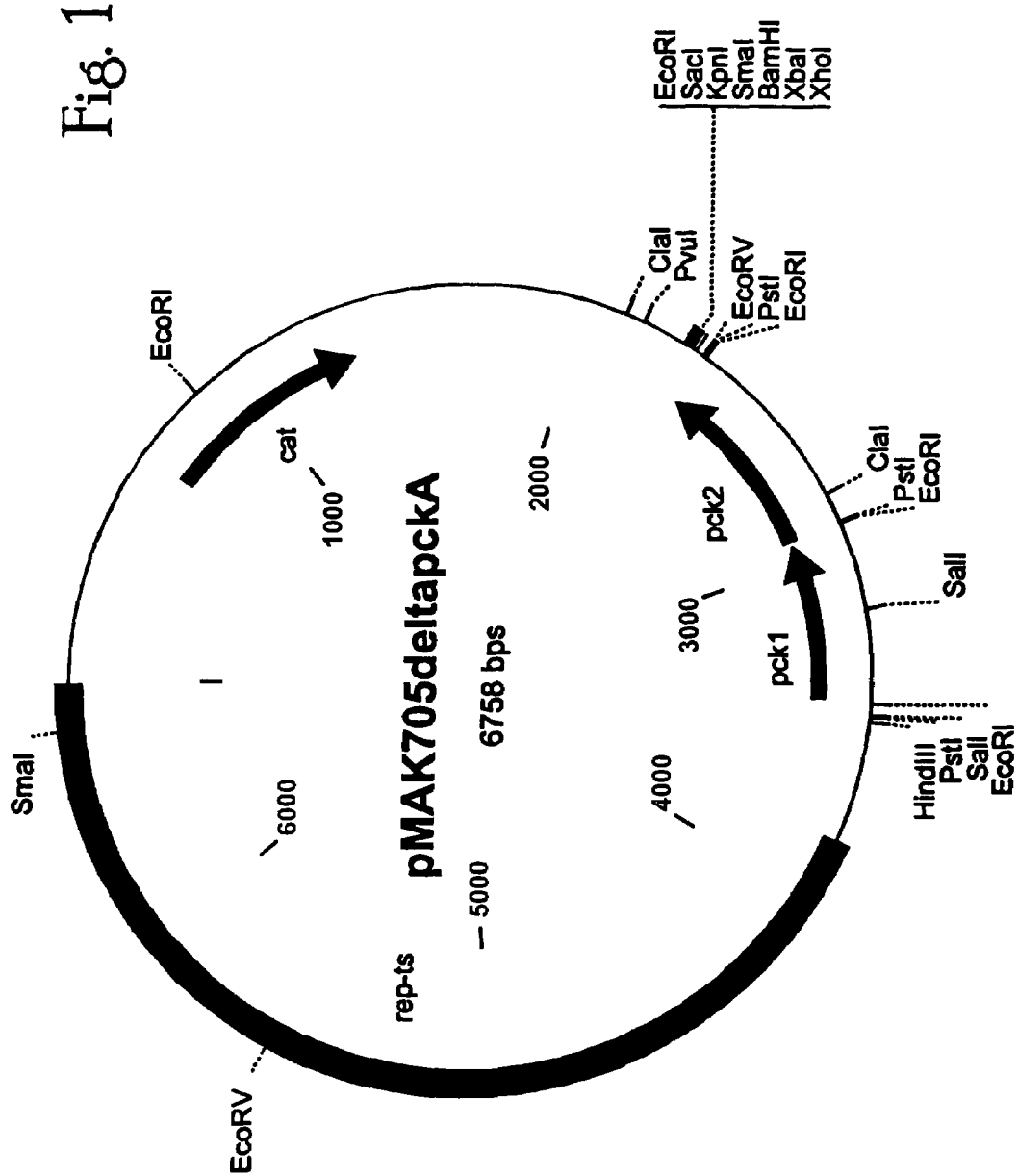
FIG. 1: pMAK705ΔpckA (=pMAK705deltapckA)

The length data are to be understood as approxroximate data. The abbreviations and designations used have the following meaning:

cat: Chloramphenicol resistance gene
rep-ts: Temperature-sensitive replication region of the plasmid pSC101
pck1: Part of the 5' region of the pckA gene
pck2: Part of the 3' region of the pckA gene
ytfP'-yjfA': DNA sequence containing truncated coding regions of ytfP and yjfA
kan: Kanamycin resistance gene
gdhA: Glutamate dehydrogenase gene
rhtC: Threonine resistance-imparting gene The abbreviations for the restriction enzymes have the following meaning BamHI: restriction endonuclease from *Bacillus amyloliquefaciens*
BglII: restriction endonuclease from *Bacillus globigii*
ClaI: restriction endonuclease from *Caryphanon latum*
EcoRI: restriction endonuclease from *Escherichia coli*
EcoRV: restriction endonuclease from *Escherichia coli*
HindIII: restriction endonuclease from *Haemophilus influenzae*
KpnI: restriction endonuclease from *Klebsiella pneumoniae*
PstI: restriction endonuclease from *Providencia stuartii*
PvuI: restriction endonuclease from *Proteus vulgaris*
SacI: restriction endonuclease from *Streptomyces achromogenes*
SalI: restriction endonuclease from *Streptomyces albus*
SmaI: restriction endonuclease from *Serratia marcescens*
XbaI: restriction endonuclease from *Xanthomonas badrii*
XhoI: restriction endonuclease from *Xanthomonas holcicola*

DETAILED DESCRIPTION OF THE INVENTION

Where L-amino acids or amino acids are mentioned in the following, this means one or more amino acids, including their salts, chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan, L-homoserine and L-arginine. L-Threonine is particularly preferred.

In this context the term "attenuation" describes the reduction or switching-off, in a microorganism, of the intracellular activity of one or more enzymes (proteins) which are coded for by the appropriate DNA, for example by using a weak promoter or a gene or allele which codes for an appropriate enzyme with low activity, or inactivating the appropriate enzyme (protein), and optionally combining these measures.

By attenuation measures, the activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism.

The process is characterized in that the following steps are carried out:

a) fermentation of microorganisms of the family Enterobacteriaceae in which at least the pckA gene is attenuated, b) enrichment of the appropriate L-amino acid in the medium or in the cells of the microorganisms of the family Enterobacteriaceae, and c) isolation of the desired L-amino acid.

The microorganisms provided by the present invention can produce L-amino acids from glucose, sucrose, lactose, fructose, maltose, molasses, optionally starch or optionally cellulose, or from glycerol and ethanol. Said microorganisms are representatives of the family Enterobacteriaceae selected from the genera *Escherichia, Erwinia, Providencia* and *Serratia*. The genera *Escherichia* and *Serratia* are preferred. The species *Escherichia coli* and *Serratia marcescens* may be mentioned in particular among the genera *Escherichia* and *Serratia* respectively.

Examples of suitable strains, particularly L-threonine-producing strains, of the genus *Escherichia*, especially of the species *Escherichia coli*, are:

*Escherichia coli* TF427
*Escherichia coli* H4578
*Escherichia coli* KY10935
*Escherichia coli* VNIIgenetika MG442
*Escherichia coli* VNIIgenetika M1
*Escherichia coli* VNIIgenetika 472T23
*Escherichia coli* BKIIM B-3996
*Escherichia coli* kat 13
*Escherichia coli* KCCM-10132.

Examples of suitable L-threonine-producing strains of the genus *Serratia*, especially of the species *Serratia marcescens*, are:

*Serratia marcescens* HNr21
*Serratia marcescens* TLr156
*Serratia marcescens* T2000.

L-Threonine-producing strains of the family Enterobacteriaceae preferably possess, inter alia, one or more genetic or phenotypic characteristics selected from the group comprising resistance to α-amino-β-hydroxyvaleric acid, resistance to thialysine, resistance to ethionine, resistance to α-methylserine, resistance to diaminosuccinic acid, resistance to α-aminobutyric acid, resistance to borrelidine, resistance to rifampicin, resistance to valine analogues such as valine hydroxamate, resistance to purine analogues such as 6-dimethylaminopurine, need for L-methionine, optionally partial and compensable need for L-isoleucine, need for meso-diaminopimelic acid, auxotrophy in respect of threonine-containing dipeptides, resistance to L-threonine, resistance to L-homoserine, resistance to L-lysine, resistance to L-methionine, resistance to L-glutamic acid, resistance to L-aspartate, resistance to L-leucine, resistance to L-phenylalanine, resistance to L-serine, resistance to L-cysteine, resistance to L-valine, sensitivity to fluoropyruvate, defective threonine dehydrogenase, optionally capability for sucrose utilization, amplification of the threonine operon, amplification of homoserine dehydrogenase I-aspartate kinase I, preferably of the feedback-resistant form, amplification of homoserine kinase, amplification of threonine synthase, amplification of aspartate kinase, optionally of the feedback-resistant form, amplification of aspartate semialdehyde dehydrogenase, amplification of phosphoenolpyruvate carboxylase, optionally of the feedback-resistant form, amplification of phosphoenolpyruvate synthase, amplification of transhydrogenase, amplification of the RhtB gene product, amplification of the RhtC gene product, amplification of the YfiK gene product, amplification of malate quinone oxidoreductase and amplification of a pyruvate carboxylase and attenuation of acetic acid formation.

It has been found that the production of L-amino acids, especially L-threonine, by microorganisms of the family Enterobacteriaceae is improved after attenuation and, in particular, switching-off of the pckA gene coding for PEP carboxykinase (EC 4.1.1.49).

The nucleotide sequence of the pcka gene of *Escherichia coli* has been published by Medina et al. (Journal of Bacteriology 172, 7151-7156 (1990)) and can also be taken from the genome sequence of *Escherichia coli* published by Blattner et al. (Science 277, 1453-1462 (1997)). The nucleotide sequence of the pckA gene of *Escherichia coli* is represented in SEQ ID No. 1 and the amino acid sequence of the corresponding gene product is represented in SEQ ID No. 2.

The pckA genes described in the above literature references can be used according to the invention. It is also possible to use alleles of the pckA gene which result from the degeneracy of the genetic code or from neutral sense mutations.

Attenuation can be achieved for example by reducing or switching off the expression of the pcka gene or the catalytic properties of the enzyme protein. Both measures may optionally be combined.

Gene expression can be reduced by an appropriate culture technique, by genetic modification (mutation) of the signal structures of gene expression, or by means of antisense RNA technology. Examples of signal structures of gene expression are repressor genes, activator genes, operators, promoters, attenuators, ribosome binding sites, the start codon and terminators. Those skilled in the art will find relevant information inter alia in e.g. Jensen and Hammer (Biotechnology and Bioengineering 58, 191-195 (1998)), Carrier and Keasling (Biotechnology Progress 15, 58-64 (1999)), Franch and Gerdes (Current Opinion in Microbiology 3, 159-164 (2000)) and well-known textbooks on genetics and molecular biology, for example the textbook by Knippers ("Molekulare Genetik" ("Molecular Genetics"), 6th edition, Georg Thieme Verlag, Stuttgart, Germany, 1995) or the textbook by Winnacker ("Gene und Klone" ("From Genes to Clones"), VCH Verlagsgesellschaft, Weinheim, Germany, 1990).

Mutations which cause a change or reduction in the catalytic properties of enzyme proteins are known from the state of the art. Examples which may be mentioned are the studies of Qiu and Goodman (Journal of Biological Chemistry 272, 8611-8617 (1997)), Yano et al. (Proceedings of the National Academy of Sciences USA 95, 5511-5515 (1998)) and Wente and Schachmann (Journal of Biological Chemistry 266, 20833-20839 (1991)). Surveys can be found in well-known textbooks on genetics and molecular biology, e.g. the textbook by Hagemann ("Allgemeine Genetik" ("General Genetics"), Gustav Fischer Verlag, Stuttgart, 1986).

Mutations to be taken into consideration are transitions, transversions, insertions and deletions. Depending on the effect of amino acid exchange on the enzyme activity, the term missense mutations or nonsense mutations is used. Insertions or deletions of at least one base pair in a gene cause frame shift mutations, the result of which is that false amino acids are incorporated or translation is terminated prematurely. Deletions of several codons typically lead to a complete loss of enzyme activity. Instructions for the production of such mutations form paft of the state of the art and can be found in well-known textbooks on genetics and molecular biology, e.g. the textbook by Knippers ("Molekulare Genetik" ("Molecular Genetics"), 6th edition, Georg Thieme Verlag, Stuttgart, Germany, 1995), the textbook by Winnacker ("Gene und Klone" ("From Genes to Clones"), VCH Verlagsgesellschaft, Weinheim, Germany, 1990) or the textbook by Hagemann ("Allgemeine Genetik" ("General Genetics"), Gustav Fischer Verlag, Stuttgart, 1986).

An example of a plasmid by means of which the pckA gene of *Escherichia coli* can be attenuated and, in particular, switched off by position-specific mutagenesis is plasmid pMAK705ΔpckA (FIG. 1). It contains only part of the 5' region and part of the 3' region of the pckA gene. A 349 bp segment of the coding region is missing (deletion). The sequence of this DNA, which can be used for mutagenesis of the pckA gene, is represented in SEQ ID No. 3.

The deletion mutation of the pckA gene can be incorporated into suitable strains by gene or allele exchange.

A common method is the method of gene exchange using a conditionally replicating pSC101 derivative, pMAK705, as described by Hamilton et al. (Journal of Bacteriology 174, 4617-4622 (1989)). Other methods described in the state of the art, for example that of Martinez-Morales et al. (Journal of Bacteriology, 7143-7148 (1999)) or that of Boyd et al. (Journal of Bacteriology 182, 842-847 (2000)), can also be used.

When exchange has been carried out, the form of the ΔpckA allele represented in SEQ ID No. 4, which is a further subject of the invention, is present in the strain in question.

Mutations in the pckA gene or mutations involving expression of the pckA gene can also be transferred to different strains by conjugation or transduction.

Furthermore, for the production of L-amino acids, especially L-threonine, with strains of the family Enterobacteriaceae, it can be advantageous not only to attenuate the pckA gene but also to amplify one or more enzymes of the known threonine biosynthetic pathway, or enzymes of the anaplerotic metabolism, or enzymes for the production of reduced nicotinamide adenine dinucleotide phosphate.

In this context the term "amplification" describes the increase in the intracellular activity, in a microorganism, of one or more enzymes or proteins which are coded for by the appropriate DNA, for example by increasing the copy number of the gene(s), using a strong promoter or using a gene coding for an appropriate enzyme or protein with a high activity, and optionally combining these measures.

By amplification measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on that of the wild-type protein or the activity or concentration of the protein in the starting microorganism.

Thus, for example, one or more genes selected from the group comprising:
  the thrABC operon coding for aspartate kinase, homoserine dehydrogenase, homoserine kinase and threonine synthase (U.S. Pat. No. 4,278,765),
  the pyc gene coding for pyruvate carboxylase DE-A-19 831 609),
  the pps gene coding for phosphoenolpyruvate synthase (Molecular and General Genetics 231, 332 (1992)),
  the ppc gene coding for phosphoenolpyruvate carboxylase (Gene 31, 279-283 (1984)),
  the pntA and pntB genes coding for transhydrogenase (European Journal of Biochemistry 158, 647-653 (1986)),
  the rhtB gene for homoserine resistance (EP-A-0994190), and
  the rhtC gene for threonine resistance (EP-A-1013765),
  the gdhA gene coding for glutamate dehydrogenase (Gene 27:193-199 (1984))

can be simultaneously amplified and, in particular, overexpressed.

Furthermore, for the production of L-amino acids, especially L-threonine, it can be advantageous not only to attenuate the pckA gene but also to attenuate and, in particular, switch off one or more genes selected from the group comprising:
  the tdh gene coding for threonine dehydrogenase (Ravnikar and Somerville, Journal of Bacteriology 169, 4716-4721 (1987)),
  the mdh gene coding for malate dehydrogenase (EC 1.1.1.37) (Vogel et al., Archives in Microbiology 149, 36-42 (1987)),
  the gene product of the open reading frame (orf) yjfA (Accession Number AAC77180 of the National Center for Biotechnology Information (NCBI, Bethesda, Md., USA) and SEQ ID No. 5), and
  the gene product of the open reading frame (orf) ytfP (Accession Number AAC77179 of the National Center for Biotechnology Information (NCBI, Bethesda, Md., USA) and SEQ ID No. 5), or to reduce the expression.

It is preferred to attenuate the open reading frame yjfA and/or the open reading frame ytfP.

It is also possible according to the invention to attenuate the open reading frames yjfA and/or ytfp independently of the pckA gene, in order to achieve an improvement in the amino acids, in particular L-threonine production.

The invention accordingly also provides a process, characterized in that the following steps are carried out:
  d) fermentation of microorganisms of the Enterobacteriaceae family in which at least the open reading frame yjfA and/or ytfP is attenuated,
  e) enrichment of the L-amino acid in the medium or in the cells of the microorganisms of the Enterobacteriaceae family, and
  f) isolation of the L-threonine, constituents of the fermentation broth and the biomass in its entirety or portions thereof optionally being isolated as a solid product together with the L-amino acid.

Figure 2:
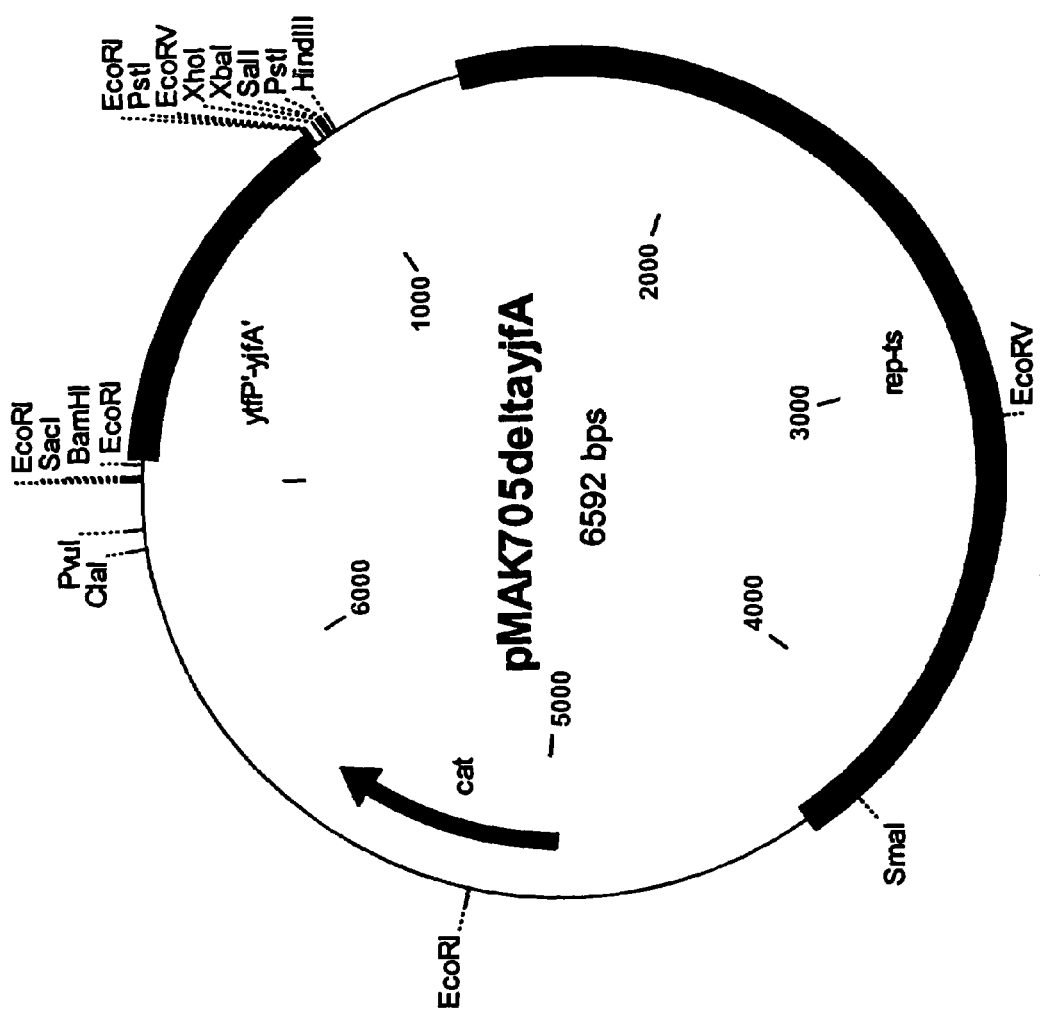
FIG. 2: pMAK705ΔyjfA (=pMAK705deltayjfA)

An example of a plasmid by means of which the open reading frames yjfA and ytfP of *Escherichia coli* can be attenuated and, in particular, switched off by position-specific mutagenesis is plasmid pMAK705ΔyjfA (FIG. 2). It contains only the 5' and 3' flanks of the ytfP-yjfA region, including very short residues of the open reading frames yjfA and ytfp. A 337 bp long part of the ytfP-yjfA region is missing (deletion). The sequence of this DNA, which can be used for mutagenesis of the ytfP-yjfA region, is represented in SEQ ID No. 6.

Figure 5:
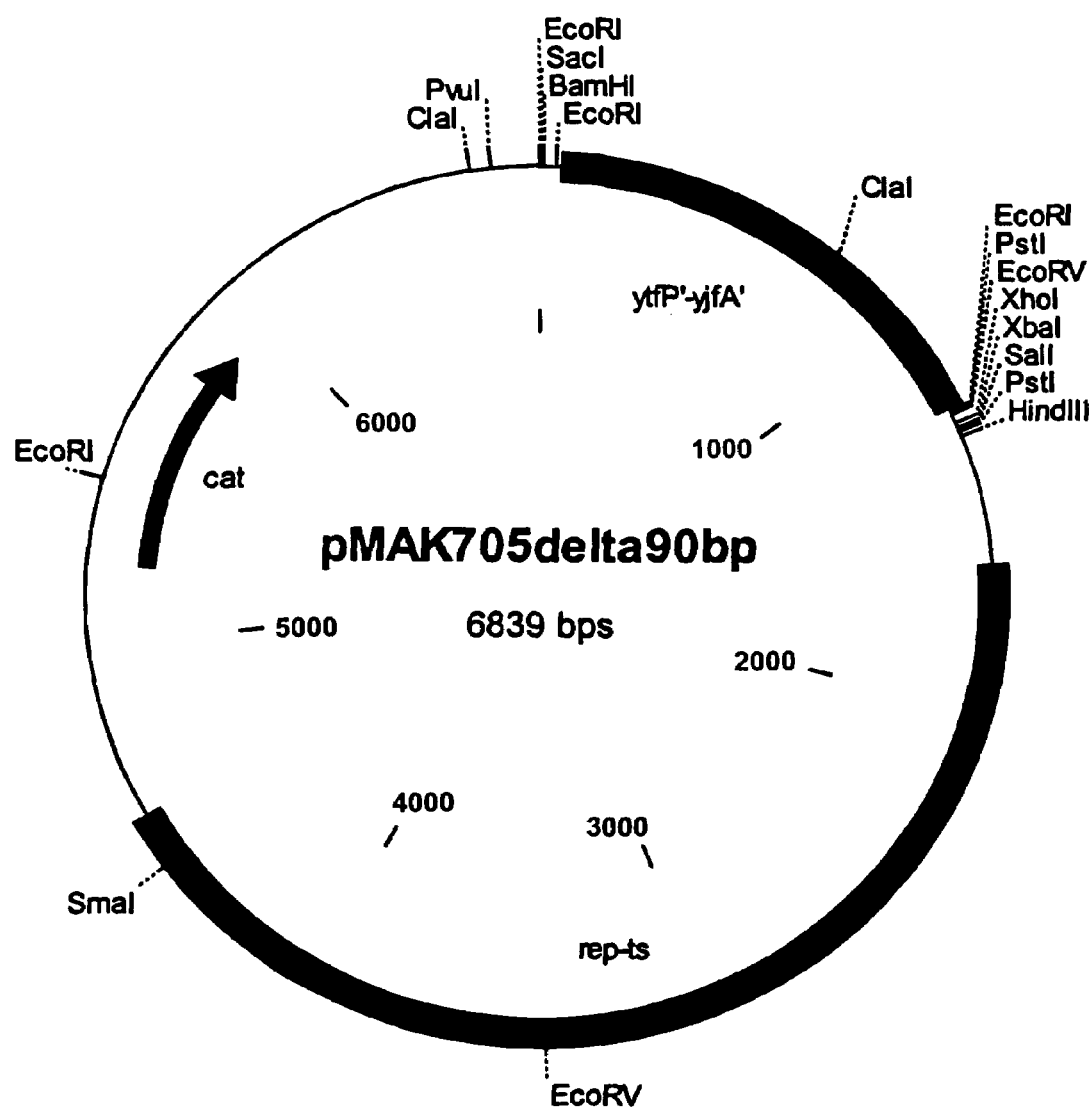
FIG. 5: pMAK705Δ90bp (=pMAK705delta90bp)

An further example of a plasmid by means of which the open reading frames yjfA and ytfP of *Escherichia coli* can be attenuated and, in particular, switched off by position-specific mutagenesis is the plasmid pMAK705Δ90bp (FIG. 5). It also contains only the 5' and 3l flanks of the ytfP-yjfA region including very short residues of the open reading frames yjfA and ytfp. A 90 bp long part of the ytfP-yjfA region is missing (deletion). The sequence of this DNA, which can be used for mutagenesis of the ytfP-yjfA region, is represented in SEQ ID No. 7.

This deletion mutation can be incorporated into suitable strains by gene or allele replacement. It is also possible to transfer mutations in the open reading frames yjfA and/or ytfP or mutations affecting expression of these open reading frames into various strains by conjugation or transduction.

When replacement has been carried out, the form of the ΔytfP and ΔyjfA allele represented in SEQ ID No. 6 or SEQ ID No. 7, which are a further subject of the invention, is present in the strain in question.

Furthermore, for the production of L-amino acids, especially L-threonine, it can be advantageous, in addition to the individual or joint attenuation of the pckA gene or of the open reading frames yjfA and/or ytfP, to switch off undesired secondary reactions (Nakayama: "Breeding of Amino Acid Producing Microorganisms", in: Overproduction of Microbial Products, Krumphanzl, Sikyta, Vanek (eds.), Academic Press, London, UK, 1982).

The microorganisms prepared according to the invention can be cultivated by the batch process or the fed batch process. A summary of known cultivation methods is provided in the textbook by Chmiel (Bioprozesstechnik 1. Einführung in die Bioverfahrenstechnik (Bioprocess Technology 1. Introduction to Bioengineering) (Gustav Fischer Verlag, Stuttgart, 1991)) or in the textbook by Storhas (Bioreaktoren und periphere Einrichtungen (Bioreactors and Peripheral Equipment) (Vieweg Verlag, Brunswick/Wiesbaden, 1994)).

The culture medium to be used must appropriately meet the demands of the particular strains. Descriptions of culture media for various microorganisms can be found in the handbook "Manual of Methods for General Bacteriology" of the American Society for Bacteriology (Washington D.C., USA, 1981).

Carbon sources which can be used are sugars and carbohydrates, e.g. glucose, sucrose, lactose, fructose, maltose, molasses, starch and optionally cellulose, oils and fats, e.g. soya oil, sunflower oil, groundnut oil and coconut fat, fatty acids, e.g. palmitic acid, stearic acid and linoleic acid, alcohols, e.g. glycerol and ethanol, and organic acids, e.g. acetic acid. These substances can be used individually or as a mixture.

Nitrogen sources which can be used are organic nitrogen-containing compounds such as peptones, yeast extract, meat extract, malt extract, corn steep liquor, soya bean flour and urea, or inorganic compounds such as ammonium sulfate, ammonium chloride, ammonium phosphate, ammonium carbonate and ammonium nitrate. The nitrogen sources can be used individually or as a mixture.

Phosphorus sources which can be used are phosphoric acid, potassium dihydrogenphosphate or dipotassium hydrogenphosphate or the corresponding sodium salts. The culture medium must also contain metal salts, e.g. magnesium sulfate or iron sulfate, which are necessary for growth. Finally, essential growth-promoting substances such as amino acids and vitamins can be used in addition to the substances mentioned above. Suitable precursors can also be added to the culture medium. Said feed materials can be added to the culture all at once or fed in appropriately during cultivation.

The pH of the culture is controlled by the appropriate use of basic compounds such as sodium hydroxide, potassium hydroxide, ammonia or aqueous ammonia, or acid compounds such as phosphoric acid or sulfuric acid. Foaming can be controlled using antifoams such as fatty acid polyglycol esters. The stability of plasmids can be maintained by adding suitable selectively acting substances, e.g. antibiotics, to the medium. Aerobic conditions are maintained by introducing oxygen or oxygen-containing gaseous mixtures, e.g. air, into the culture. The temperature of the culture is normally 25° C. to 45° C. and preferably 30° C. to 40° C. The culture is continued until the formation of L-amino acids or L-threonine has reached a maximum. This objective is normally achieved within 10 hours to 160 hours.

L-Amino acids can be analyzed by means of anion exchange chromatography followed by ninhydrin derivation, as described by Spackman et al. (Analytical Chemistry 30, 1190 (1958)), or by reversed phase HPLC, as described by Lindroth et al. (Analytical Chemistry 51, 1167-1174 (1979)).

A pure culture of the *Escherichia coli* K-12 strain DH5α/pMAK705 was deposited on $8^{th}$ Sep. 2000 at the Deutsche Sammlung für Mikroorganismen und Zellkulturen GmbH (DSM), Mascheroder Weg 1B, D-3300 Braunschweig, Germany (DSMZ=German Collection of Microorganisms and Cell Cultures, Braunschweig, Germany) in accordance with the Budapest Treaty as DSM 13720.

A pure culture of the *Escherichia coli* K-12 strain MG442ΔpckA was deposited on $2^{nd}$ Oct. 2000 at the Deutsche Sammlung für Mikroorganismen und Zellkulturen GmbH (DSM), Mascheroder Weg 1B, D-3300 Braunschweig, Germany (DSMZ=German Collection of Microorganisms and Cell Cultures, Braunschweig, Germany) in accordance with the Budapest Treaty as DSM 13761.

A pure culture of the *Escherichia coli* K-12 strain B-3996kurΔtdhΔpckA/pVIC40 was deposited on $9^{th}$ Mar. 2001 at the Deutsche Sammlung für Mikroorganismen und Zellkulturen GmbH (DSM), Mascheroder Weg 1B, D-3300 Braunschweig, Germany (DSMZ=German Collection of Microorganisms and Cell Cultures, Braunschweig, Germany) in accordance with the Budapest Treaty as DSM 14150.

A pure culture of the *Escherichia coli* K-12 strain MG442Δ90yjfA was deposited on $9^{th}$ May 2001 at the Deutsche Sammlung für Mikroorganismen und Zellkulturen GmbH (DSM), Mascheroder Weg 1B, D-3300 Braunschweig, Germany (DSMZ=German Collection of Microorganisms and Cell Cultures, Braunschweig, Germany) in accordance with the Budapest Treaty as DSM 14289.

It is also possible according to the invention individually to attenuate the open reading frames ytfP and yjfA in order to improve the production of L-amino acids.

The process according to the invention is used for the preparation of L-amino acids, e.g. L-threonine, L-isoleucine, L-methionine, L-homoserine and L-lysine, especially L-threonine, by fermentation.

The present invention is illustrated in greater detail below with the aid of Examples.

The isolation of plasmid DNA from *Escherichia coli* and all the techniques for restriction, Klenow treatment and alkaline phosphatase treatment were carried out as described by Sambrook et al. (Molecular cloning—A laboratory manual (1989), Cold Spring Harbor Laboratory Press). Unless indicated otherwise, the transformation of *Escherichia coli* was carried out as described by Chung et al. (Proceedings of the National Academy of Sciences USA 86, 2172-2175 (1989)).

The incubation temperature for the preparation of strains and transformants was 37° C. Temperatures of 30° C. and 44° C. were used in the gene exchange process of Hamilton et al.

EXAMPLE 1

Construction of the Deletion Mutation of the pckA Gene

Parts of the 5' and 3' regions of the pckA gene of *Escherichia coli* K12 were amplified using the polymerase chain reaction (PCR) and synthetic oligonucleotides. The nucleotide sequence of the pckA gene in *E. coli* K12 MG1655 (SEQ ID No. 1) was used to synthesize the following PCR primers (MWG Biotech, Ebersberg, Germany):

```
pckA'5'-1:    5' - GATCCGAGCCTGACAGGTTA - 3'
              (SEQ ID NO:8)

pckA'5'-2:    5' - GCATGCGCTCGGTCAGGTTA - 3'
              (SEQ ID NO:9)

pckA'3'-1:    5' - AGGCCTGAAGATGGCACTATCG - 3'
              (SEQ ID NO:10)

pckA'3'-2:    5' - CCGGAGAAGCGTAGGTGTTA - 3'.
              (SEQ ID NO:11)
```

The chromosomal E. coli K12 MG1655 DNA used for the PCR was isolated with "Qiagen Genomic-tips 100/G" (QIAGEN, Hilden, Germany) according to the manufacturer's instructions. An approx. 500 bp DNA fragment from the 5' region of the pckA gene (denoted as pck1) and an approx. 600 bp DNA fragment from the 3' region of the pckA gene (denoted as pck2) could be amplified with the specific primers under standard PCR conditions (Innis et al. (1990), PCR Protocols. A Guide to Methods and Applications, Academic Press) using Taq DNA polymerase (Gibco-BRL, Eggenstein, Germany). The PCR products were each ligated with vector pCR2.1TOPO (TOPO TA Cloning Kit, Invitrogen, Groningen, The Netherlands) according to the manufacturer's instructions and transformed into E. coli strain TOP10F'. Plasmid-carrying cells were selected on LB agar containing 50 µg/ml of ampicillin. After isolation of the plasmid DNA, vector pCR2.1TOPOpck2 was cleaved with the restriction enzymes StuI and XbaI and, after separation in 0.8% agarose gel, the pck2 fragment was isolated with the aid of the QIAquick Gel Extraction Kit (QIAGEN, Hilden, Germany). After isolation of the plasmid DNA, vector pCR2.1TOPOpck1 was cleaved with the enzymes EcoRV and XbaI and ligated to the isolated pck2 fragment. The E. coli strain DH5α was transformed with the ligation mixture and plasmid-carrying cells were selected on LB agar containing 50 µg/ml of ampicillin. After isolation of the plasmid DNA, control cleavage with the enzymes SpeI and XbaI was used to detect plasmids containing, in cloned form, the mutagenic DNA sequence represented in SEQ ID No. 3. One of the plasmids was denoted as pCR2.1TOPOΔpckA.

EXAMPLE 2

Construction of Exchange Vector pMAK705ΔpckA

After restriction with the enzymes SpeI and XbaI and separation in 0.8% agarose gel, the pckA allele described in Example 1 was isolated from vector pCR2.1TOPOΔpckA and ligated to plasmid pMAK705 (Hamilton et al., Journal of Bacteriology 174, 4617-4622 (1989)) which had been digested with the enzyme XbaI. DH5α was transformed with the ligation mixture and plasmid-carrying cells were selected on LB agar containing 20 µg/ml of chloramphenicol. After isolation of the plasmid DNA and cleavage with the enzymes HpaI, KpnI, HindIII, SalI and PstI, successful cloning was detected. The exchange vector formed, pMAK705ΔpckA (=pMAK705deltapckA), is shown in FIG. 1.

EXAMPLE 3

Position-specific Mutagenesis of the pckA Gene in the E. coli Strain MG442

The L-threonine-producing E. coli strain MG442 is described in patent U.S. Pat. No. 4,278,765 and deposited in the Russian National Collection of Industrial Microorganisms (VKPM, Moscow, Russia) as CMIM B-1628.

The strain MG442 has a resistance to α-amino-β-hydroxyvaleric acid and has an optionally partial and compensable need for L-isoleucine.

For exchange of the chromosomal pckA gene for the plasmid-coded deletion construct, MG442 was transformed with plasmid pMAK705ΔpckA. The gene exchange was carried out by the selection method described by Hamilton et al. (Journal of Bacteriology 174, 4617-4622 (1989)) and was verified by standard PCR methods (Innis et al. (1990), PCR Protocols. A Guide to Methods and Applications, Academic Press) using the following oligonucleotide primers:

```
pckA'5'-1:    5' - GATCCGAGCCTGACAGGTTA - 3'
              (SEQ ID NO:8)

pckA'3'-2:    5' - CCGGAGAAGCGTAGGTGTTA - 3'
              (SEQ ID NO:11)
```

The strain obtained was denoted as MG442ΔpckA.

EXAMPLE 4

Preparation of L-threonine with the Strain MG442ΔpckA

MG442ΔpckA was cultivated on minimum medium of the following composition: 3.5 g/l of $Na_2HPO_4.2H_2O$, 1.5 g/l of $KH_2PO_4$, 1 g/l of $NH_4Cl$, 0.1 g/l of $MgSO_4.7H_2O$, 2 g/l of glucose and 20 g/l of agar. The formation of L-threonine was checked in 10 ml batch cultures contained in 100 ml Erlenmeyer flasks. These were inoculated with 10 ml of a preculture medium of the following composition: 2 g/l of yeast extract, 10 g/l of $(NH_4)_2SO_4$, 1 g/l of $KH_2PO_4$, 0.5 g/l of $MgSO_4.7H_2O$, 15 g/l of $CaCO_3$ and 20 g/l of glucose, and incubated for 16 hours at 37° C. and 180 rpm on an ESR incubator from Kühner AG (Birsfelden, Switzerland). 250 µl of this preculture were transferred to 10 ml of a production medium (25 g/l of $(NH_4)_2SO_4$, 2 g/l of $KH_2PO_4$, 1 g/l of $MgSO_4.7H_2O$, 0.03 g/l of $FeSO_4.7H_2O$, 0.018 g/l of $MnSO_4.1H_2O$, 30 g/l of $CaCO_3$, 20 g/l of glucose) and incubated for 48 hours at 37° C. After incubation, the optical density (OD) of the culture suspension was determined with an LP2W photometer from Dr. Lange (Berlin, Germany) at a measurement wavelength of 660 nm.

The concentration of L-threonine formed was then determined in the sterile-filtered culture supernatant with an amino acid analyzer from Eppendorf-BioTronik (Hamburg, Germany) by means of ion exchange chromatography and post-column reaction with ninhydrin detection.

The result of the experiment is shown in Table 1.

TABLE 1

| Strain | OD (660 nm) | L-Threonine g/l |
|---|---|---|
| MG442 | 6.0 | 1.5 |
| MG442ΔpckA | 5.4 | 3.7 |

EXAMPLE 5

Preparation of L-threonine with the Strain MG442ΔpckA/pMW218gdhA 5.1 Amplification and Cloning of the gdhA Gene The glutamate dehydrogenase gene from Escherichia coli K12 is amplified using the polymerase chain reaction (PCR) and synthetic oligonucleotides. Starting from the nucleotide sequence for the gdhA gene in E. coli K12 MG1655 (gene library: Accession No. AE000270 and No. AE000271) PCR primers are synthesized (MWG Biotech, Ebersberg, Germany):

```
Gdh1:     5' - TGAACACTTCTGGCGGTACG - 3'
          (SEQ ID NO:12)

Gdh2:     5' - CCTCGGCGAAGCTAATATGG - 3'
          (SEQ ID NO:13)
```

The chromosomal *E. coli* K12 MG1655 DNA employed for the PCR is isolated according to the manufacturers instructions with "QIAGEN Genomic-tips 100/G" (QIAGEN, Hilden, Germany). A DNA fragment approx. 2150 bp in size, which comprises the gdhA coding region and approx. 350 bp 5'-flanking and approx. 450 bp 3'-flanking sequences, can be amplified with the specific primers under standard PCR conditions (Innis et al.: PCR Protocols. A Guide to Methods and Applications, 1990, Academic Press) with the Pfu-DNA polymerase (Promega Corporation, Madison, USA). The PCR product is cloned in the plasmid pCR2.1TOPO and transformed in the *E. coli* strain TOP10 (Invitrogen, Leek, The Netherlands, Product Description TOPO TA Cloning Kit, Cat. No. K4500-01). Successful cloning is demonstrated by cleavage of the plasmid pCR2.1TOPOgdhA with the restriction enzymes EcoRI and EcoRV. For this, the plasmid DNA is isolated by means of the "QIAprep Spin Plasmid Kits" (QIAGEN, Hilden, Germany) and, after cleavage, separated in a 0.8% agarose gel.

5.2 Cloning of the gdhA Gene in the Plasmid Vector pMW218

The plasmid pCR2.1TOPOgdhA is cleaved with the enzyme EcoRI, the cleavage batch is separated on 0.8% agarose gel and the gdhA fragment 2.1 kbp in size is isolated with the aid of the "QIAquick Gel Extraction Kit" (QIAGEN, Hilden, Germany). The plasmid pMW218 (Nippon Gene, Toyama, Japan) is cleaved with the enzyme EcoRI and ligated with the gdhA fragment. The *E. coli* strain DH5α is transformed with the ligation batch and pMW218-carrying cells are selected by plating out on LB agar (Lennox, Virology 1955, 1: 190), to which 20 µg/ml kanamycin are added.

Figure 3:
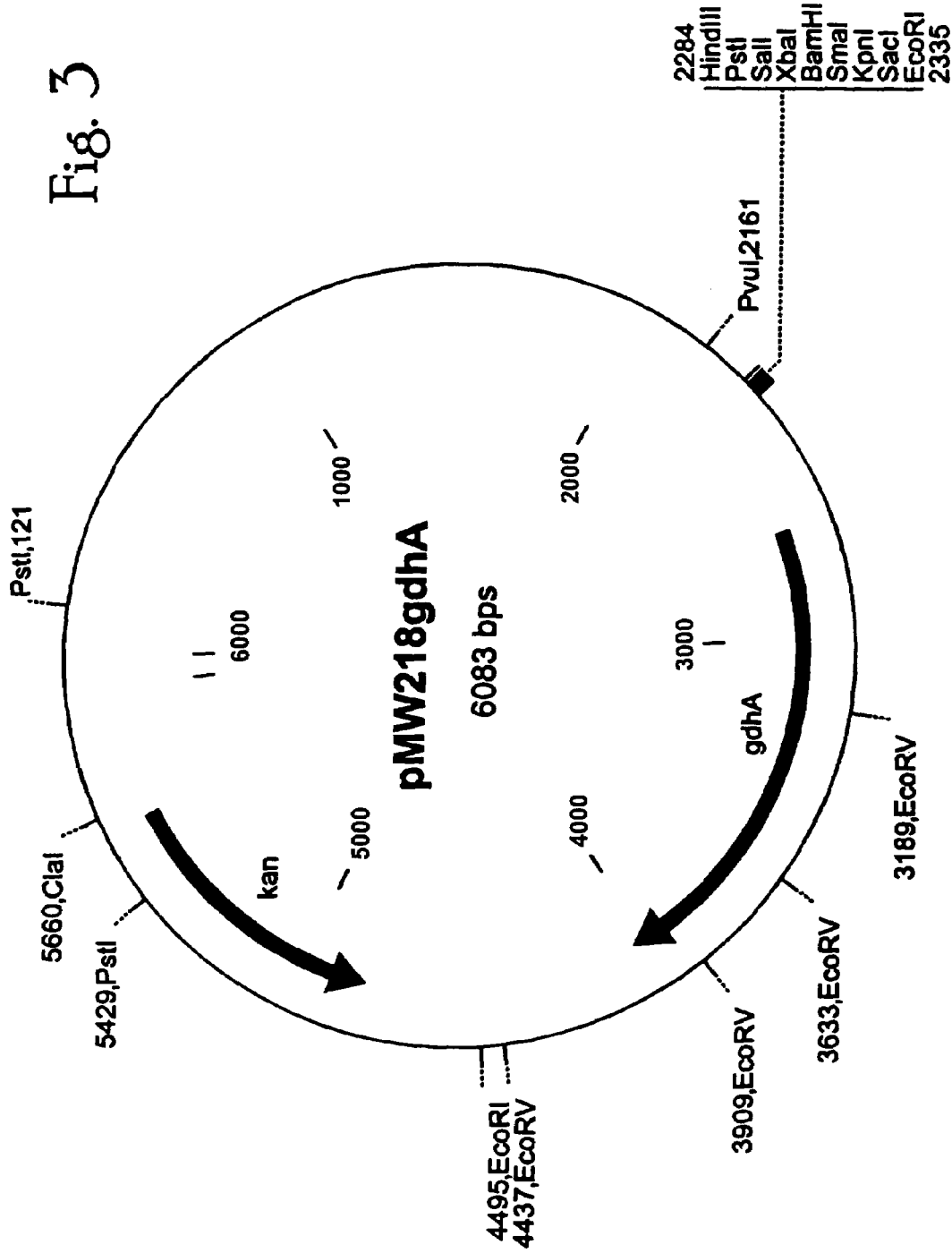
FIG. 3: pMW218gdhA

Successful cloning of the gdhA gene can be demonstrated after plasmid DNA isolation and control cleavage with EcoRI and EcoRV. The plasmid is called pMW218gdhA (FIG. 3).

5.3 Preparation of the Strain MG442ΔpckA/pMW218gdhA

The strain MG442ΔpckA obtained in Example 3 and the strain MG442 are transformed with the plasmid pMW218gdhA and transformants are selected on LB agar, which is supplemented with 20 µg/ml kanamycin. The strains MG442ΔpckA/pMW218gdhA and MG442/pMW218gdhA are formed in this manner.

5.4 Preparation of L-threonine

The preparation of L-threonine by the strains MG442ΔpckA/pMW218gdhA and MG442/pMW218gdhA is tested as described in Example 4. The minimal medium and the preculture medium are additionally supplemented with 20 µg/ml kanamycin.

The result of the experiment is summarized in Table 2.

TABLE 2

| Strain | OD (660 nm) | L-Threonine g/l |
|---|---|---|
| MG442 | 6.0 | 1.5 |
| MG442ΔpckA | 5.4 | 3.7 |
| MG442/pMW218gdhA | 5.6 | 2.6 |
| MG442ΔpckA/pMW218gdhA | 5.5 | 4.0 |

EXAMPLE 6

Preparation of L-threonine with the Strain MG442ΔpckA/pMW219rhtC 6.1 Amplification of the rhtC Gene The rhtC gene from *Escherichia coli* K12 is amplified using the polymerase chain reaction (PCR) and synthetic oligonucleotides. Starting from the nucleotide sequence for the rhtC gene in *E. coli* K12 MG1655 (gene library: Accession No. AE000458, Zakataeva et al. (FEBS Letters 452, 228-232 (1999)), PCR primers are synthesized (MWG Biotech, Ebersberg, Germany):

```
RhtC1:    5' - CTGTTAGCATCGGCGAGGCA - 3'
          (SEQ ID NO:14)

RhtC2:    5' - GCATGTTGATGGCGATGACG - 3'
          (SEQ ID NO:15)
```

The chromosomal *E. coli* K12 MG1655 DNA employed for the PCR is isolated according to the manufacturers instructions with "QIAGEN Genomic-tips 100/G" (QIAGEN, Hilden, Germany). A DNA fragment approx. 800 bp in size can be amplified with the specific primers under standard PCR conditions (Innis et al.: PCR Protocols. A Guide to Methods and Applications, 1990, Academic Press) with Pfu-DNA polymerase (Promega Corporation, Madison, USA).

6.2 Cloning of the rhtC Gene in the Plasmid Vector pMW219

Figure 4:
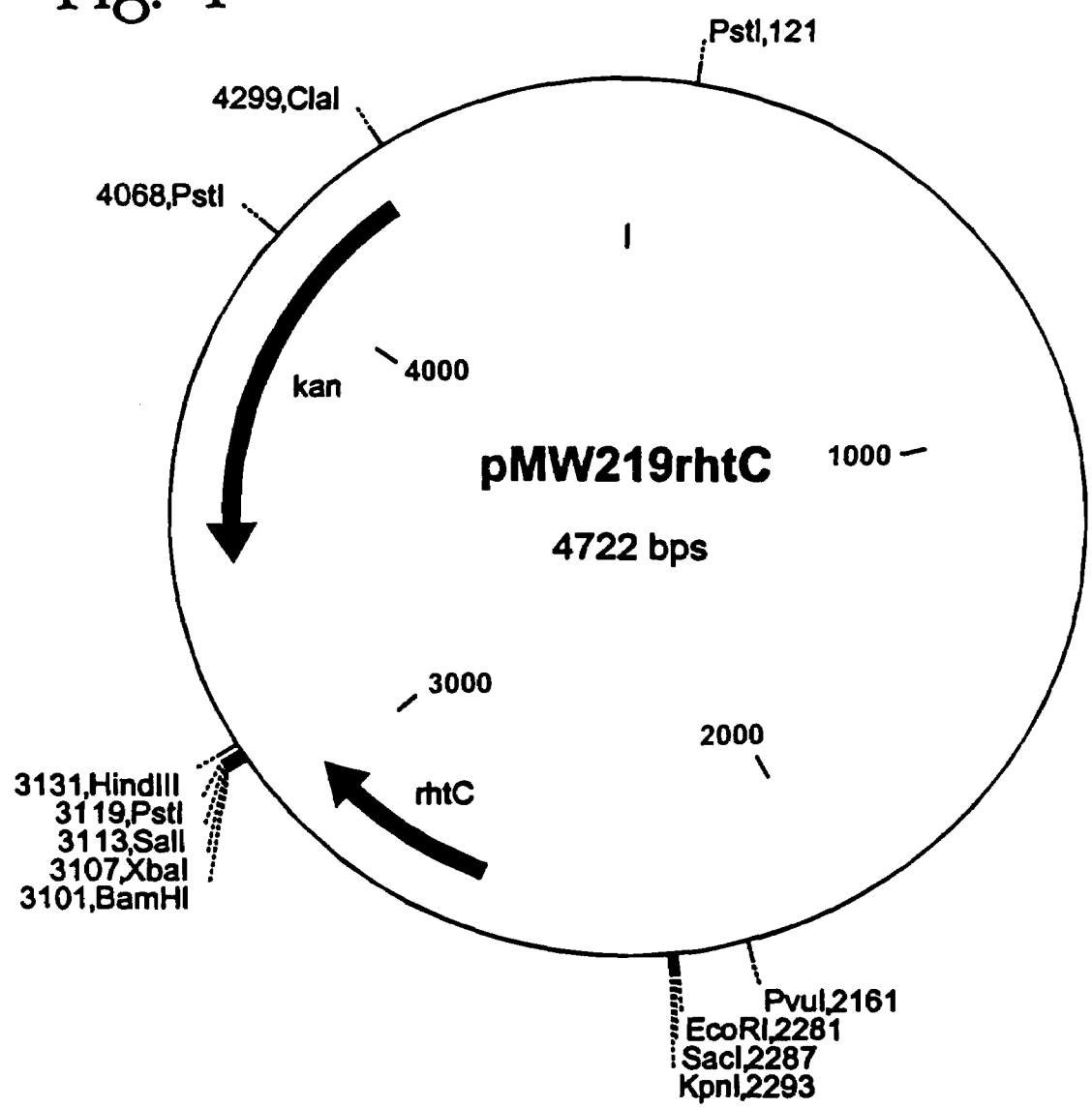
FIG. 4: pMW219rhtC

The plasmid pMW219 (Nippon Gene, Toyama, Japan) is cleaved with the enzyme SamI and ligated with the rhtC-PCR fragment. The *E. coli* strain DH5α is transformed with the ligation batch and pMW219-carrying cells are selected on LB agar, which is supplemented with 20 µg/ml kanamycin. Successful cloning can be demonstrated after plasmid DNA isolation and control cleavage with KpnI, HindIII and NcoI. The plasmid pMW219rhtC is shown in FIG. 4.

6.3 Preparation of the Strain MG442ΔpckA/pMW219rhtC

The strain MG442ΔpckA obtained in Example 3 and the strain MG442 are transformed with the plasmid pMW219rhtC and transformants are selected on LB agar, which is supplemented with 20 µg/ml kanamycin. The strains MG442ΔpckA/pMW219rhtC and MG442/pMW219rhtC are formed in this manner.

6.4 Preparation of L-threonine

The preparation of L-threonine by the strains MG442ΔpckA/pMW219rhtC and MG442/pMW219rhtC is tested as described in Example 4. The minimal medium and the preculture medium are additionally supplemented with 20 µg/ml kanamycin. The result of the experiment is summarized in Table 3.

TABLE 3

| Strain | OD (660 nm) | L-Threonine g/l |
|---|---|---|
| MG442 | 6.0 | 1.5 |
| MG442ΔpckA | 5.4 | 3.7 |
| MG442/pMW219rhtC | 5.2 | 2.9 |
| MG442ΔpckA/pMW219rhtC | 4.8 | 4.4 |

EXAMPLE 7

Preparation of L-threonine with the Strain B-3996kurΔtdhΔpckA/pVIC40

The L-threonine-producing *E. coli* strain B-3996 is described in U.S. Pat. No. 5,175,107 and deposited at the Russian National Collection for Industrial Microorganisms (VKPM, Moscow, Russia).

The strain B-3996 has, inter alia, a resistance to α-amino-β-hydroxyvaleric acid, has an attenuated, in particular switched-off, or defective threonine dehydrogenase, has an enhanced homoserine dehydrogenase I aspartate kinase I in the feed back resistant form, has an optionally partial and compensable need for L-isoleucine and has the ability to utilize sucrose.

7.1 Preparation of the Strain B-3996kurΔtdhΔpckA/pVIC40

After culture in antibiotic-free complete medium for approximately ten generations, a derivative of strain B-3996 which no longer contains the plasmid pVIC40 is isolated. The strain formed is streptomycin-sensitive and is designated B-3996kur.

The method described by Hamilton et al. (Journal of Bacteriology (1989) 171: 4617-4622), which is based on the use of the plasmid pMAK705 with a temperature-sensitive replicon, was used for incorporation of a deletion into the tdh gene. The plasmid pDR121 (Ravnikar and Somerville, Journal of Bacteriology (1987) 169:4716-4721) contains a DNA fragment from *E. coli* 3.7 kilo-base pairs (kbp) in size, on which the tdh gene is coded. To generate a deletion of the tdh gene region, pDR121 is cleaved with the restriction enzymes ClaI and EcoRV and the DNA fragment 5 kbp in size isolated is ligated, after treatment with Klenow enzyme. The ligation batch is transformed in the *E. coli* strain DH5α and plasmid-carrying cells are selected on LB agar, to which 50 µg/ml ampicillin are added.

Successful deletion of the tdh gene can be demonstrated after plasmid DNA isolation and control cleavage with EcoRI. The EcoRI fragment 1.7 kbp in size is isolated, and ligated with the plasmid pMAK705, which is partly digested with EcoRI. The ligation batch is transformed in DH5α and plasmid-carrying cells are selected on LB agar, to which 20 µg/ml chloramphenicol are added. Successful cloning is demonstrated after isolation of the plasmid DNA and cleavage with EcoRI. The pMAK705 derivative formed is designated pDM32.

For the gene replacement, B-3996kur is transformed with the plasmid pDM32. The replacement of the chromosomal tdh gene with the plasmid-coded deletion construct is carried out by the selection process described by Hamilton et al. and is verified by standard PCR methods (Innis et al. (1990), PCR Protocols. A Guide to Methods and Applications, Academic Press) with the following oligonucleotide primers:

```
Tdh1:     5'-TCGCGACCTATAAGTTTGGG-3'
          (SEQ ID NO:16)

Tdh2:     5'-AATACCAGCCCTTGTTCGTG-3'.
          (SEQ ID NO:17)
```

The strain formed is tested for kanamycin sensitivity and is designated B-3996kurΔtdh.

For the position-specific mutagenesis of the pckA gene, B-3996kurΔtdh is transformed with the replacement vector pMAK705ΔpckA described in Example 2. The replacement of the chromosomal pckA gene by the plasmid-coded deletion construct is carried out as described in Example 3. The strain obtained is called B-3996kurΔtdhΔpckA.

B-3996kurΔtdh and B-3996kurΔtdhΔpckA are transformed with the plasmid pVIC40 isolated from B-3996 and plasmid-carrying cells are selected on LB agar with 20 µg/ml streptomycin. In each case a selected individual colony is called B-3996kurΔtdh/pVIC40 and B-3996kurΔtdhΔpckA/pVIC40.

7.2 Preparation of L-threonine

The preparation of L-threonine by the strains B-3996kurΔtdh/pVIC40 and B-3996kurΔtdhΔpckA/pVIC40 is tested as described in Example 4. The minimal medium, the preculture medium and the production medium are additionally supplemented with 20 µg/ml streptomycin.

The result of the experiment is summarized in Table 4.

TABLE 4

| Strain | OD (660 nm) | L-Threonine g/l |
|---|---|---|
| B-3996kurΔtdh/pVIC40 | 4.7 | 6.26 |
| B-3996kurΔtdhΔpckA/pVIC40 | 4.9 | 8.92 |

EXAMPLE 8

Preparation of L-lysine with the Strain TOC21RΔpckA

The L-lysine-producing *E. coli* strain pDA1/TOC21R is described in the patent application F-A-2511032 and deposited at the Collection Nationale de Culture de Microorganisme (CNCM=National Microorganism Culture Collection, Pasteur Institute, Paris, France) under number I-167. The strain and the plasmid-free host are also described by Dauce-Le Reverend et al. (European Journal of Applied Microbiology and Biotechnology 15:227-231 (1982)) under the name TOCR21/pDA1.

8.1 Position-specific Mutagenesis of the pckA Gene in the *E. coli* Strain TOC21R After culture in antibiotic-free LB medium for approximately six generations, a derivative of strain pDA1/TOC21R which no longer contains the plasmid pDA1 is isolated. The strain formed is tetracycline-sensitive and is called TOC21R.

For replacement of the chromosomal pckA gene by the plasmid-coded deletion construct, TOC21R is transformed with the plasmid pMAK705ΔpckA (Example 2). The gene replacement is carried out by the selection method described by Hamilton et al. (1989) Journal of Bacteriology 174, 4617-4622) and is verified by standard PCR methods (Innis et al. (1990) PCR Protocols. A Guide to Methods and Applications, Academic Press) with the following oligonucleotide primers:

```
pckA'5'-1:    5' - GATCCGAGCCTGACAGGTTA - 3'
              (SEQ ID NO:8)

pckA'3'-2:    5' - CCGGAGAAGCGTAGGTGTTA - 3'
              (SEQ ID NO:11)
```

The strain obtained is called TOC21RΔpckA.

8.2 Preparation of L-lysine with the Strain TOC21RΔpckA

The formation of L-lysine by the strains TOC21RΔ pckA and TOC21R is checked in batch cultures of 10 ml contained in 100 ml conical flasks. For this, 10 ml of preculture medium of the following composition: 2 g/l yeast extract, 10 g/l $(NH_4)_2SO_4$, 1 g/l $KH_2PO_4$, 0.5 g/l $MgSO_4*7H_2O$, 15 g/l CaCO$_3$, 20 g/l glucose are inoculated and the batch is incubated for 16 hours at 37° C. and 180 rpm on an ESR incubator from Kühner AG (Birsfelden, Switzerland). 250 µl of this preculture are transinoculated into 10 ml of production medium (25 g/l (NH$_4$)$_2$SO$_4$, 2 g/l KH$_2$PO$_4$, 1 g/l MgSO$_4$*7H$_2$O, 0.03 g/l FeSO$_4$*7H$_2$O, 0.018 g/l MnSO$_4$*1H$_2$O, 30 g/l CaCO$_3$, 20 g/l glucose, 25 mg/l L-isoleucine and 5 mg/l thiamine) and the batch is incubated for 72 hours at 37° C. After the incubation the optical density (OD) of the culture suspension is determined with an LP2W photometer from Dr. Lange (Berlin, Germany) at a measurement wavelength of 660 nm.

The concentration of L-lysine formed is then determined in the sterile-filtered culture supernatant with an amino acid analyzer from Eppendorf-BioTronik (Hamburg, Germany) by ion exchange chromatography and post-column reaction with ninhydrin detection.

The result of the experiment is shown in Table 5.

TABLE 5

| Strain | OD (660 nm) | L-Lysine g/l |
|---|---|---|
| TOC21R | 1.0 | 1.14 |
| TOC21RΔpckA | 1.0 | 1.27 |

EXAMPLE 9

Preparation of L-isoleucine with the Strain B-3996kurΔtdhilvA$^+$ΔpckA/pVIC40

9.1 Preparation of the Strain B-3996kurΔtdhilvA$^+$ΔpckA/pVIC40

The strain B-3996kurΔtdh, which is in need of L-isoleucin, obtained in Example 7.1 is transduced with the aid of the phage P1kc (Lennox, Virology 1, 190-206 (1955); Miller, Experiments in Molecular Genetics, Cold Spring Harbor Laboratory 1972) and L-isoleucine-prototrophic transductants are isolated.

For this, the phage P1kc is multiplied on the strain MG1655 (Guyer et al., Cold Spring Harbor Symposium of Quantitative Biology 45, 135-140 (1981) and Blattner et al., Science 277, 1453-1462 (1997))and the phage lysate is employed for the transduction of the strain B-3996kurΔtdh. The multiplicity of the infection is approximately 0.2. Selection for L-isoleucine-prototrophic transductants is carried out on minimal agar, which contains 2 g/l glucose and 10 mg/l L-threonine. An L-isoleucine-prototrophic transductant is isolated, smeared on to LB agar for purification or isolation and called B-3996kurΔtdhilvA$^+$.

The pckA gene of the strain B-3996kurΔtdhilvA$^+$is then replaced, as described in Example 3, by the ΔpckA allele prepared in Example 1 and 2. The strain obtained is called B-3996kurΔtdhilvA$^+$ΔpckA.

The strains B-3996kurΔtdhilvA$^+$and B-3996kurΔtdhilvA$^+$ΔpckA are transformed with the plasmid pVIC40 isolated from strain B-3996 and plasmid-carrying cells are selected on LB agar, which is supplemented with 20 µg/ml streptomycin. In each case a selected individual colony is called B-3996kurΔtdhilvA$^+$ΔpckA/pVIC40 and B-3996kurΔtdhilvA$^+$/pVIC40.

9.2 Preparation of L-isoleucine

The preparation of L-isoleucine by the strains B-3996kurΔtdhilvA$^+$/pVIC40 and B-3996kurΔtdhilvA$^+$ΔpckA/pVIC40 is tested under the test conditions as described in Example 4. The minimal medium, the preculture medium and the production medium are additionally supplemented with 20 µg/ml streptomycin.

The result of the experiment is shown in Table 6.

TABLE 6

| Strain | OD (660 nm) | L-Isoleucine mg/l |
|---|---|---|
| B-3996kurΔtdhilvA$^+$/pVIC40 | 5.8 | 57 |
| B-3996kurΔtdhilvA$^+$ΔpckA/pVIC40 | 5.7 | 70 |

EXAMPLE 10

Preparation of L-valine with the Strain B-12288ΔpckA

The L-valine-producing E. coli strain AJ 11502 is described in the patent specification U.S. Pat. No. 4,391,907 and deposited at the National Center for Agricultural Utilization Research (Peoria, Ill., USA) as NRRL B-12288.

10.1 Position-specific Mutagenesis of the pckA Gene in the E. coli Strain B-1288

After culture in antibiotic-free LB medium for approximately six generations, a plasmid-free derivative pf strain AJ 11502 is isolated. The strain formed is ampicillin-sensitive and is called AJ11502kur.

For replacement of the chromosomal pckA gene by the plasmid-coded deletion construct, AJ11502kur is transformed with the plasmid pMAK705ΔpckA (see Example 2). The gene replacement is carried out by the selection method described by Hamilton et al. (1989) Journal of Bacteriology 174, 4617-4622) and is verified by standard PCR methods (Innis et al. (1990) PCR Protocols. A Guide to Methods and Applications, Academic Press) with the following oligonucleotide primers:

```
pckA'5'-1:    5' - GATCCGAGCCTGACAGGTTA - 3'
              (SEQ ID NO:8)

pckA'3'-2:    5' - CCGGAGAAGCGTAGGTGTTA - 3'
              (SEQ ID NO:11)
```

The strain obtained is called AJ11502kurΔpckA. The plasmid described in the patent specification U.S. Pat. No. 4,391,907, which carries the genetic information in respect of valine production, is isolated from strain NRRL B-12288. The strain AJ11502kurΔpckA is transformed with this plasmid. One of the transformants obtained is called B-12288ΔpckA.

10.2 Preparation of L-valine with the Strain B-12288ΔpckA

The formation of L-valine by the strains B-12288ΔpckA and NRRL B-12288 is checked in batch cultures of 10 ml contained in 100 ml conical flasks. For this, 10 ml of preculture medium of the following composition: 2 g/l yeast extract, 10 g/l (NH$_4$)$_2$SO$_4$, 1 g/l KH$_2$PO$_4$, 0.5 g/l MgSO$_4$*7H$_2$O, 15 g/l CaCO$_3$, 20 g/l glucose and 50 mg/l ampicillin are inoculated and the batch is incubated for 16 hours at 37° C. and 180 rpm on an ESR incubator from Küthner AG (Birsfelden, Switzerland). 250 µl of this preculture are transinoculated into 10 ml of production medium (25 g/l (NH$_4$)$_2$SO$_4$, 2 g/l KH$_2$PO$_4$, 1 g/l MgSO$_4$*7H$_2$O, 0.03 g/l FeSO$_4$*7H$_2$O, 0.018 g/l MnSO$_4$*1H$_2$O, 30 g/l CaCO$_3$, 20 g/l glucose, 5 mg/l thiamine and 50 mg/l ampicillin) and the batch is incubated for 72 hours at 37° C. After the incubation the optical density (OD) of the culture suspension is determined with an LP2W photometer from Dr. Lange (Berlin, Germany) at a measurement wavelength of 660 nm.

The concentration of L-valine formed is then determined in the sterile-filtered culture supernatant with an amino acid analyzer from Eppendorf-BioTronik (Hamburg, Germany) by ion exchange chromatography and post-column reaction with ninhydrin detection.

The result of the experiment is shown in Table 7.

TABLE 7

| Strain | OD (660 nm) | L-Valine g/l |
|---|---|---|
| NRRL B-12288 | 5.6 | 0.93 |
| B-12288ΔpckA | 5.5 | 1.12 |

EXAMPLE 11

Construction of Deletion Mutations of the ytfP-yjfA Gene Region

The ytfP-yjfA gene region is amplified from *Escherichia coli* K12 using the polymerase chain reaction (PCR) and synthetic oligonucleotides. Starting from the nucleotide sequence of the ytfP-yjfA gene region in *E. coli* K12 MG1655 (SEQ ID No. 5), the following PCR primers are synthesized (MWG Biotech, Ebersberg, Germany):

```
ytfP-1:    5' - GGCGATGTCGCAACAAGCTG - 3'
           (SEQ ID NO:18)

ytfP-2:    5' - CTGTTCATGGCCGCTTGCTG - 3'
           (SEQ ID NO:19)
```

The chromosomal *E. coli* K12 MG1655 DNA employed for the PCR is isolated according to the manufacturers instructions with "Qiagen Genomic-tips 100/G" (QIAGEN, Hilden, Germany). A DNA fragment approx. 1300 bp in size can be amplified with the specific primers under standard PCR conditions (Innis et al. (1990) PCR Protocols. A Guide to Methods and Applications, Academic Press) with Taq-DNA polymerase (Gibco-BRL, Eggenstein, Germany). The PCR product is ligated with the vector pCR2.1TOPO (TOPO TA Cloning Kit, Invitrogen, Groningen, The Netherlands) in accordance with the manufacturers instructions and transformed into the E. coli strain TOP10F'. Selection of plasmid-carrying cells takes place on LB agar, to which 50 μg/ml ampicillin are added. After isolation of the plasmid DNA, successful cloning of the PCR product is checked with the restriction enzymes EcoRI and NsiI.

To generate a 337 bp deletion in the yftP-yjfA region, the vector pCR2.1TOPOytfP-yjfA is cleaved with the restriction enzymes NdeI and SspI and the DNA fragment 4.8 kbp in size is ligated, after treatment with Klenow enzyme.

To generate a 90 bp deletion, the vector pCR2.1TOPOytfP-yjfA is cleaved with the enzymes NdeI and SpII and the DNA fragment 5 kbp in size is ligated, after treatment with Klenow enzyme.

The *E. coli* strain DH5α is transformed with the ligation batches and plasmid-carrying cells are selected on LB agar, to which 50 μg/ml ampicillin is added. After isolation of the plasmid DNA those plasmids in which the mutagenic DNA sequence shown in SEQ ID No. 6 and SEQ ID No. 7 is cloned are detected by control cleavage with the enzyme EcoRI. The plasmids are called pCR2.1TOPOΔyjfA and pCR2.1TOPOΔ90bp.

EXAMPLE 12

Construction of the Replacement Vectors pMAK705ΔyjfA and pMAK705Δ90bp

The ytfP-yjfA alleles described in Example 11 are isolated from the vectors pCR2.1TOPOΔyjfA and pCR2.1TOPOΔ90bp after restriction with the enzymes SacI and XbaI and separation in 0.8% agarose gel, and ligated with the plasmid pMAK705 (Hamilton et al. (1989) Journal of Bacteriology 174, 4617-4622), which is digested with the enzymes SacI and XbaI. The ligation batches are transformed in DH5α and plasmid-carrying cells are selected on LB agar, to which 20 μg/ml chloramphenicol are added. Successful cloning is demonstrated after isolation of the plasmid DNA and cleavage with the enzymes SacI and XbaI. The replacement vectors formed, pMAK705ΔyjfA (=pMAK705deltayjfA) and pMAK705Δ90bp (=pMAK705delta90bp), are shown in FIG. 2 and in FIG. 5.

EXAMPLE 13

Position-specific Mutagenesis of the ytfP-yjfA Gene Region in the *E. coli* Strain MG442

For replacement of the chromosomal ytfP-yjfA gene region with the plasmid-coded 90 bp deletion construct, MG442 is transformed with the plasmid pMAK705Δ90bp, The gene replacement is carried out by the selection method described by Hamilton et al. (1989) Journal of Bacteriology 174, 4617-4622) and is verified by standard PCR methods (Innis et al. (1990) PCR Protocols. A Guide to Methods and Applications, Academic Press) with the following oligonucleotide primers:

```
ytfP-1:    5' - GGCGATGTCGCAACAAGCTG - 3'
           (SEQ ID NO:18)

ytfP-2:    5' - CTGTTCATGGCCGCTTGCTG - 3'
           (SEQ ID NO:19)
```

The strain obtained is called MG442Δ90yjfA.

EXAMPLE 14

Preparation of L-threonine with the Strain MG442Δ90yjfA

The preparation of L-threonine by the strain MG442Δ90yjfA is tested as described in Example 4. The result of the experiment is summarized in Table 8.

TABLE 8

| Strain | OD (660 nm) | L-Threonine g/l |
|---|---|---|
| MG442 | 6.0 | 1.5 |
| MG442Δ90yjfA | 5.7 | 2.1 |

EXAMPLE 15

Preparation of L-threonine with the Strain MG442Δ90yjfAΔpckA

15.1 Preparation of the Strain MG442Δ90yjfAΔpckA

The pckA gene of the strain MG442Δ90yjfA is replaced, as described in Example 3, by the ΔpckA allele (see Example 1 and 2). The strain obtained is called MG442Δ90yjfAΔpckA.

15.2 Preparation of L-threonine

The preparation of L-threonine with the strain MG442Δ90yjfAΔpckA is carried out as described in Example 4. The result is shown in Table 9.

TABLE 9

| Strain | OD (660 nm) | L-Threonine g/l |
|---|---|---|
| MG442Δ90yjfA | 5.7 | 2.1 |
| MG442Δ90yjfAΔpckA | 5.3 | 3.9 |

---

What is claimed is:

1. A fermentation process suitable for the preparation of a desired L-amino acid selected from the group consisting of L-threonine, L-isoleucine, L-valine, and L-lysine, wherein the following steps are carried out:

a) fermentation of an *E. coli* strain in a fermentation broth for producing the desired L-amino acid, wherein the endogenous ytfP-yjfA gene region of *E.coli* is inactivated by one or more methods of mutagenesis selected from the group consisting of deletion, insertional mutagenesis due to homologous recombination, and transition or transversion mutagenesis with incorporation of a non-sense mutation in the ytfP-yjfA gene region, and b) concentration of the fermentation broth to eliminate water and increase the concentration of said L-amino acid, and c) isolation of the L-amino acid.

2. The process according to claim 1, wherein one or more *E. coli* genes selected from the group consisting of:

(a) the thrABC operon coding for aspartate kinase, homoserine dehydrogenase, homoserine kinase and threonine synthase, (b) the pps gene coding for phosphoenolpyruvate synthase, (c) the ppc gene coding for phosphoenolpyruvate carboxylase, (d) the pntA and pntB genes coding for transhydrogenase, (e) the rhtB gene for homoserine resistance, (f) the rhtC gene for threonine resistance, and (g) the gdhA gene coding for glutamate dehydrogenase are overexpressed by increasing the copy number or placed under a strong promoter during fermentation for the preparation of said L-amino acids.

3. The process according to claim 1, wherein one or more *E. coli* genes selected from the group consisting of:

(a) the tdh gene coding for threonine dehydrogenase, and (b) the mdh gene coding for malate dehydrogenase are inactivated by one or more methods of mutagenesis selected from the group consisting of deletion, insertional mutagenesis due to homologous recombination, and transition or transversion mutagenesis with incorporation of a non-sense mutation in said *E. coli* genes.

4. The process of claim 1, wherein constituents of the fermentation broth and the biomass in its entirety or portions thereof are isolated as a solid product together with said L-amino acid.

5. The process according to claim 1, wherein L-threonine is produced by fermenting the *E. coli* strain MG442Δ90yjfA deposited under DSM14289.

* * * * *

SEQUENCE LISTING

<160> NUMBER OF SEQ ID NOS: 19

<210> SEQ ID NO 1
<211> LENGTH: 1623
<212> TYPE: DNA
<213> ORGANISM: Escherichia coli
<220> FEATURE:
<221> NAME/KEY: CDS
<222> LOCATION: (1)..(1620)
<223> OTHER INFORMATION: pckA

<400> SEQUENCE: 1

```
atg cgc gtt aac aat ggt ttg acc ccg caa gaa ctc gag gct tat ggt      48
Met Arg Val Asn Asn Gly Leu Thr Pro Gln Glu Leu Glu Ala Tyr Gly
 1               5                  10                  15 atc agt gac gta cat gat atc gtt tac aac cca agc tac gac ctg ctg      96
Ile Ser Asp Val His Asp Ile Val Tyr Asn Pro Ser Tyr Asp Leu Leu
             20                  25                  30 tat cag gaa gag ctc gat ccg agc ctg aca ggt tat gag cgc ggg gtg     144
Tyr Gln Glu Glu Leu Asp Pro Ser Leu Thr Gly Tyr Glu Arg Gly Val
         35                  40                  45 tta act aat ctg ggt gcc gtt gcc gtc gat acc ggg atc ttc acc ggt     192
Leu Thr Asn Leu Gly Ala Val Ala Val Asp Thr Gly Ile Phe Thr Gly
     50                  55                  60 cgt tca cca aaa gat aag tat atc gtc cgt gac gat acc act cgc gat     240
Arg Ser Pro Lys Asp Lys Tyr Ile Val Arg Asp Asp Thr Thr Arg Asp
 65                  70                  75                  80 act ttc tgg tgg gca gac aaa ggc aaa ggt aag aac gac aac aaa cct     288
Thr Phe Trp Trp Ala Asp Lys Gly Lys Gly Lys Asn Asp Asn Lys Pro
                 85                  90                  95 ctc tct ccg gaa acc tgg cag cat ctg aaa ggc ctg gtg acc agg cag     336
Leu Ser Pro Glu Thr Trp Gln His Leu Lys Gly Leu Val Thr Arg Gln
            100                 105                 110 ctt tcc ggc aaa cgt ctg ttc gtt gtc gac gct ttc tgt ggt gcg aac     384
Leu Ser Gly Lys Arg Leu Phe Val Val Asp Ala Phe Cys Gly Ala Asn
        115                 120                 125 ccg gat act cgt ctt tcc gtc cgt ttc atc acc gaa gtg gcc tgg cag     432
Pro Asp Thr Arg Leu Ser Val Arg Phe Ile Thr Glu Val Ala Trp Gln
    130                 135                 140 gcg cat ttt gtc aaa aac atg ttt att cgc ccg agc gat gaa gaa ctg     480
Ala His Phe Val Lys Asn Met Phe Ile Arg Pro Ser Asp Glu Glu Leu
145                 150                 155                 160 gca ggt ttc aaa cca gac ttt atc gtt atg aac ggc gcg aag tgc act     528
Ala Gly Phe Lys Pro Asp Phe Ile Val Met Asn Gly Ala Lys Cys Thr
                165                 170                 175 aac ccg cag tgg aaa gaa cag ggt ctc aac tcc gaa aac ttc gtg gcg     576
Asn Pro Gln Trp Lys Glu Gln Gly Leu Asn Ser Glu Asn Phe Val Ala
            180                 185                 190
```

```
ttt aac ctg acc gag cgc atg cag ctg att ggc ggc acc tgg tac ggc      624
Phe Asn Leu Thr Glu Arg Met Gln Leu Ile Gly Gly Thr Trp Tyr Gly
        195                 200                 205 ggc gaa atg aag aaa ggg atg ttc tcg atg atg aac tac ctg ctg ccg      672
Gly Glu Met Lys Lys Gly Met Phe Ser Met Met Asn Tyr Leu Leu Pro
210                 215                 220 ctg aaa ggt atc gct tct atg cac tgc tcc gcc aac gtt ggt gag aaa      720
Leu Lys Gly Ile Ala Ser Met His Cys Ser Ala Asn Val Gly Glu Lys
225                 230                 235                 240 ggc gat gtt gcg gtg ttc ttc ggc ctt tcc ggc acc ggt aaa acc acc      768
Gly Asp Val Ala Val Phe Phe Gly Leu Ser Gly Thr Gly Lys Thr Thr
                245                 250                 255 ctt tcc acc gac ccg aaa cgt cgc ctg att ggc gat gac gaa cac ggc      816
Leu Ser Thr Asp Pro Lys Arg Arg Leu Ile Gly Asp Asp Glu His Gly
            260                 265                 270 tgg gac gat gac ggc gtg ttt aac ttc gaa ggc ggc tgc tac gca aaa      864
Trp Asp Asp Asp Gly Val Phe Asn Phe Glu Gly Gly Cys Tyr Ala Lys
        275                 280                 285 act atc aag ctg tcg aaa gaa gcg gaa cct gaa atc tac aac gct atc      912
Thr Ile Lys Leu Ser Lys Glu Ala Glu Pro Glu Ile Tyr Asn Ala Ile
    290                 295                 300 cgt cgt gat gcg ttg ctg gaa aac gtc acc gtg cgt gaa gat ggc act      960
Arg Arg Asp Ala Leu Leu Glu Asn Val Thr Val Arg Glu Asp Gly Thr
305                 310                 315                 320 atc gac ttt gat gat ggt tca aaa acc gag aac acc cgc gtt tct tat     1008
Ile Asp Phe Asp Asp Gly Ser Lys Thr Glu Asn Thr Arg Val Ser Tyr
                325                 330                 335 ccg atc tat cac atc gat aac att gtt aag ccg gtt tcc aaa gcg ggc     1056
Pro Ile Tyr His Ile Asp Asn Ile Val Lys Pro Val Ser Lys Ala Gly
            340                 345                 350 cac gcg act aag gtt atc ttc ctg act gct gat gct ttc ggc gtg ttg     1104
His Ala Thr Lys Val Ile Phe Leu Thr Ala Asp Ala Phe Gly Val Leu
        355                 360                 365 ccg ccg gtt tct cgc ctg act gcc gat caa acc cag tat cac ttc ctc     1152
Pro Pro Val Ser Arg Leu Thr Ala Asp Gln Thr Gln Tyr His Phe Leu
    370                 375                 380 tct ggc ttc acc gcc aaa ctg gcc ggt act gag cgt ggc atc acc gaa     1200
Ser Gly Phe Thr Ala Lys Leu Ala Gly Thr Glu Arg Gly Ile Thr Glu
385                 390                 395                 400 ccg acg cca acc ttc tcc gct tgc ttc ggc gcg gca ttc ctg tcg ctg     1248
Pro Thr Pro Thr Phe Ser Ala Cys Phe Gly Ala Ala Phe Leu Ser Leu
                405                 410                 415 cac ccg act cag tac gca gaa gtg ctg gtg aaa cgt atg cag gcg gcg     1296
His Pro Thr Gln Tyr Ala Glu Val Leu Val Lys Arg Met Gln Ala Ala
            420                 425                 430 ggc gcg cag gct tat ctg gtt aac act ggc tgg aac ggc act ggc aaa     1344
Gly Ala Gln Ala Tyr Leu Val Asn Thr Gly Trp Asn Gly Thr Gly Lys
        435                 440                 445 cgt atc tcg att aaa gat acc cgc gcc att atc gac gcc atc ctc aac     1392
Arg Ile Ser Ile Lys Asp Thr Arg Ala Ile Ile Asp Ala Ile Leu Asn
    450                 455                 460 ggt tcg ctg gat aat gca gaa acc ttc act ctg ccg atg ttt aac ctg     1440
Gly Ser Leu Asp Asn Ala Glu Thr Phe Thr Leu Pro Met Phe Asn Leu
465                 470                 475                 480 gcg atc cca acc gaa ctg ccg ggc gta gac acg aag att ctc gat ccg     1488
Ala Ile Pro Thr Glu Leu Pro Gly Val Asp Thr Lys Ile Leu Asp Pro
                485                 490                 495 cgt aac acc tac gct tct ccg gaa cag tgg cag gaa aaa gcc gaa acc     1536
Arg Asn Thr Tyr Ala Ser Pro Glu Gln Trp Gln Glu Lys Ala Glu Thr
            500                 505                 510
```

```
ctg gcg aaa ctg ttt atc gac aac ttc gat aaa tac acc gac acc cct      1584
Leu Ala Lys Leu Phe Ile Asp Asn Phe Asp Lys Tyr Thr Asp Thr Pro
        515                 520                 525 gcg ggt gcc gcg ctg gta gcg gct ggt ccg aaa ctg taa                  1623
Ala Gly Ala Ala Leu Val Ala Ala Gly Pro Lys Leu
        530                 535                 540

<210> SEQ ID NO 2
<211> LENGTH: 540
<212> TYPE: PRT
<213> ORGANISM: Escherichia coli

<400> SEQUENCE: 2

Met Arg Val Asn Asn Gly Leu Thr Pro Gln Glu Leu Glu Ala Tyr Gly
  1               5                  10                  15

Ile Ser Asp Val His Asp Ile Val Tyr Asn Pro Ser Tyr Asp Leu Leu
             20                  25                  30

Tyr Gln Glu Glu Leu Asp Pro Ser Leu Thr Gly Tyr Glu Arg Gly Val
         35                  40                  45

Leu Thr Asn Leu Gly Ala Val Ala Val Asp Thr Gly Ile Phe Thr Gly
     50                  55                  60

Arg Ser Pro Lys Asp Lys Tyr Ile Val Arg Asp Asp Thr Thr Arg Asp
 65                  70                  75                  80

Thr Phe Trp Trp Ala Asp Lys Gly Lys Gly Lys Asn Asp Asn Lys Pro
                 85                  90                  95

Leu Ser Pro Glu Thr Trp Gln His Leu Lys Gly Leu Val Thr Arg Gln
            100                 105                 110

Leu Ser Gly Lys Arg Leu Phe Val Val Asp Ala Phe Cys Gly Ala Asn
        115                 120                 125

Pro Asp Thr Arg Leu Ser Val Arg Phe Ile Thr Glu Val Ala Trp Gln
    130                 135                 140

Ala His Phe Val Lys Asn Met Phe Ile Arg Pro Ser Asp Glu Glu Leu
145                 150                 155                 160

Ala Gly Phe Lys Pro Asp Phe Ile Val Met Asn Gly Ala Lys Cys Thr
                165                 170                 175

Asn Pro Gln Trp Lys Glu Gln Gly Leu Asn Ser Glu Asn Phe Val Ala
            180                 185                 190

Phe Asn Leu Thr Glu Arg Met Gln Leu Ile Gly Gly Thr Trp Tyr Gly
        195                 200                 205

Gly Glu Met Lys Lys Gly Met Phe Ser Met Met Asn Tyr Leu Leu Pro
    210                 215                 220

Leu Lys Gly Ile Ala Ser Met His Cys Ser Ala Asn Val Gly Glu Lys
225                 230                 235                 240

Gly Asp Val Ala Val Phe Phe Gly Leu Ser Gly Thr Gly Lys Thr Thr
                245                 250                 255

Leu Ser Thr Asp Pro Lys Arg Arg Leu Ile Gly Asp Asp Glu His Gly
            260                 265                 270

Trp Asp Asp Asp Gly Val Phe Asn Phe Glu Gly Gly Cys Tyr Ala Lys
        275                 280                 285

Thr Ile Lys Leu Ser Lys Glu Ala Glu Pro Glu Ile Tyr Asn Ala Ile
    290                 295                 300

Arg Arg Asp Ala Leu Leu Glu Asn Val Thr Val Arg Glu Asp Gly Thr
305                 310                 315                 320

Ile Asp Phe Asp Asp Gly Ser Lys Thr Glu Asn Thr Arg Val Ser Tyr
                325                 330                 335
```

```
Pro Ile Tyr His Ile Asp Asn Ile Val Lys Pro Val Ser Lys Ala Gly
            340                 345                 350

His Ala Thr Lys Val Ile Phe Leu Thr Ala Asp Ala Phe Gly Val Leu
        355                 360                 365

Pro Pro Val Ser Arg Leu Thr Ala Asp Gln Thr Gln Tyr His Phe Leu
    370                 375                 380

Ser Gly Phe Thr Ala Lys Leu Ala Gly Thr Glu Arg Gly Ile Thr Glu
385                 390                 395                 400

Pro Thr Pro Thr Phe Ser Ala Cys Phe Gly Ala Ala Phe Leu Ser Leu
                405                 410                 415

His Pro Thr Gln Tyr Ala Glu Val Leu Val Lys Arg Met Gln Ala Ala
            420                 425                 430

Gly Ala Gln Ala Tyr Leu Val Asn Thr Gly Trp Asn Gly Thr Gly Lys
        435                 440                 445

Arg Ile Ser Ile Lys Asp Thr Arg Ala Ile Ile Asp Ala Ile Leu Asn
    450                 455                 460

Gly Ser Leu Asp Asn Ala Glu Thr Phe Thr Leu Pro Met Phe Asn Leu
465                 470                 475                 480

Ala Ile Pro Thr Glu Leu Pro Gly Val Asp Thr Lys Ile Leu Asp Pro
                485                 490                 495

Arg Asn Thr Tyr Ala Ser Pro Glu Gln Trp Gln Glu Lys Ala Glu Thr
            500                 505                 510

Leu Ala Lys Leu Phe Ile Asp Asn Phe Asp Lys Tyr Thr Asp Thr Pro
        515                 520                 525

Ala Gly Ala Ala Leu Val Ala Ala Gly Pro Lys Leu
    530                 535                 540

<210> SEQ ID NO 3
<211> LENGTH: 1156
<212> TYPE: DNA
<213> ORGANISM: Escherichia coli
<220> FEATURE:
<221> NAME/KEY: misc_feature
<222> LOCATION: (1)..(1156)
<223> OTHER INFORMATION: Mutagene DNA
<220> FEATURE:
<221> NAME/KEY: misc_feature
<222> LOCATION: (1)..(35)
<223> OTHER INFORMATION: Technical DNA/residues of the polylinker
      sequence
<220> FEATURE:
<221> NAME/KEY: misc_feature
<222> LOCATION: (36)..(522)
<223> OTHER INFORMATION: Part of the 5' region (pck1) of the pckA gene
<220> FEATURE:
<221> NAME/KEY: misc_feature
<222> LOCATION: (523)..(542)
<223> OTHER INFORMATION: Technical DNA/residues of the polylinker
      sequence
<220> FEATURE:
<221> NAME/KEY: misc_feature
<222> LOCATION: (543)..(1105)
<223> OTHER INFORMATION: Part of the 3' region (pck2) of the pckA gene
<220> FEATURE:
<221> NAME/KEY: misc_feature
<222> LOCATION: (1106)..(1156)
<223> OTHER INFORMATION: Technical DNA/residues of the polylinker
      sequence

<400> SEQUENCE: 3
ctagtaacgg ccgccagtgt gctggaattc ggcttgatcc gagcctgaca ggttatgagc      60
gcggggtgtt aactaatctg ggtgccgttg ccgtcgatac cggatcttc accggtcgtt     120 caccaaaaga taagtatatc gtccgtgacg ataccactcg cgatactttc tggtgggcag     180
```

```
acaaaggcaa aggtaagaac gacaacaaac ctctctctcc ggaaacctgg cagcatctga      240
aaggcctggt gaccaggcag ctttccggca aacgtctgtt cgttgtcgac gctttctgtg      300
gtgcgaaccc ggatactcgt ctttccgtcc gtttcatcac cgaagtggcc tggcaggcgc      360
attttgtcaa aaacatgttt attcgcccga gcgatgaaga actggcaggt ttcaaaccag      420
actttatcgt tatgaacggc gcgaagtgca ctaacccgca gtggaaagaa cagggtctca      480
actccgaaaa cttcgtggcg tttaacctga ccgagcgcat gcaagccgaa ttctgcagat      540
cctgaagatg gcactatcga ctttgatgat ggttcaaaaa ccgagaacac ccgcgtttct      600
tatccgatct atcacatcga taacattgtt aagccggttt ccaaagcggg ccacgcgact      660
aaggttatct tcctgactgc tgatgctttc ggcgtgttgc cgccggtttc tcgcctgact      720
gccgatcaaa cccagtatca cttcctctct ggcttcaccg ccaaactggc cggtactgag      780
cgtggcatca ccgaaccgac gccaaccttc tccgcttgct tcggcgcggc attcctgtcg      840
ctgcacccga ctcagtacgc agaagtgctg gtgaaacgta tgcaggcggc gggcgcgcag      900
gcttatctgg ttaacactgg ctggaacggc actggcaaac gtatctcgat taaagatacc      960
cgcgccatta tcgacgccat cctcaacggt tcgctggata tgcagaaaac cttcactctg     1020
ccgatgttta acctggcgat cccaaccgaa ctgccgggcg tagacacgaa gattctcgat     1080
ccgcgtaaca cctacgcttc tccggaagcc gaattctgca gatatccatc acactggcgg     1140
ccgctcgagc atgcat                                                    1156

<210> SEQ ID NO 4
<211> LENGTH: 1294
<212> TYPE: DNA
<213> ORGANISM: Escherichia coli
<220> FEATURE:
<221> NAME/KEY: misc_feature
<222> LOCATION: (1)..(3)
<223> OTHER INFORMATION: Start codon of the delta pckA allele
<220> FEATURE:
<221> NAME/KEY: misc_feature
<222> LOCATION: (1)..(598)
<223> OTHER INFORMATION: 5' region of the delta pckA allele
<220> FEATURE:
<221> NAME/KEY: misc_feature
<222> LOCATION: (599)..(618)
<223> OTHER INFORMATION: Technical DNA/residues of the polylinker
      sequence
<220> FEATURE:
<221> NAME/KEY: misc_feature
<222> LOCATION: (619)..(1291)
<223> OTHER INFORMATION: 3' region of the delta pckA allele
<220> FEATURE:
<221> NAME/KEY: misc_feature
<222> LOCATION: (1292)..(1294)
<223> OTHER INFORMATION: Stop codon of the delta pckA allele

<400> SEQUENCE: 4
atgcgcgtta caatggtttt gaccccgcaa gaactcgagg cttatggtat cagtgacgta       60
catgatatcg tttacaaccc aagctacgac ctgctgtatc aggaagagct cgatccgagc      120
ctgacaggtt atgagcgcgg ggtgttaact aatctgggtg ccgttgccgt cgataccggg      180
atcttcaccg tcgttcacc aaaagataag tatatcgtcc gtgacgatac cactcgcgat      240
actttctggt gggcagacaa aggcaaaggt aagaacgaca caaacctct ctctccggaa      300 acctggcagc atctgaaagg cctggtgacc aggcagcttt ccggcaaacg tctgttcgtt      360
gtcgacgctt tctgtggtgc gaaccccggat actcgtctttt ccgtccgttt catcaccgaa      420
gtggcctggc aggcgcattt tgtcaaaaac atgtttattc gcccgagcga tgaagaactg      480
```

-continued

```
gcaggtttca aaccagactt tatcgttatg aacggcgcga agtgcactaa cccgcagtgg      540
aaagaacagg gtctcaactc cgaaaacttc gtggcgttta acctgaccga gcgcatgcaa      600
gccgaattct gcagatcctg aagatggcac tatcgacttt gatgatggtt caaaaaccga      660
gaacacccgc gtttcttatc cgatctatca catcgataac attgttaagc cggtttccaa      720
agcgggccac gcgactaagg ttatcttcct gactgctgat gctttcggcg tgttgccgcc      780
ggtttctcgc ctgactgccg atcaaaccca gtatcacttc ctctctggct tcaccgccaa      840
actggccggt actgagcgtg gcatcaccga accgacgcca accttctccg cttgcttcgg      900
cgcggcattc ctgtcgctgc acccgactca gtacgcagaa gtgctggtga acgtatgca       960 ggcggcgggc gcgcaggctt atctggttaa cactggctgg aacggcactg caaacgtat     1020 ctcgattaaa gataccgcgc cattatcga cgccatcctc aacggttcgc tggataatgc     1080
agaaaccttc actctgccga tgtttaacct ggcgatccca accgaactgc cgggcgtaga    1140
cacgaagatt ctcgatccgc gtaacaccta cgcttctccg gaacagtggc aggaaaaagc    1200
cgaaaccctg gcgaaactgt ttatcgacaa cttcgataaa tacaccgaca ccctgcggg     1260 tgccgcgctg gtagcggctg gtccgaaact gtaa                                1294
```

<210> SEQ ID NO 5
<211> LENGTH: 1248
<212> TYPE: DNA
<213> ORGANISM: Escherichia coli
<220> FEATURE:
<221> NAME/KEY: gene
<222> LOCATION: (376)..(714)
<223> OTHER INFORMATION: ORF ytfP
<220> FEATURE:
<221> NAME/KEY: gene
<222> LOCATION: (461)..(727)
<223> OTHER INFORMATION: ORF yjfA

<400> SEQUENCE: 5

```
ggcgatgtcg caacaagctg ccttgtctta tttgctacgt ggacaagggc tggagagcga      60
tcagagcgac agtgcggcaa tgacctcgat gctgattggt ttgggggttg cgcaaagtgg     120
ccagattgtg ggtaaaatcg gcgagacgtt tggcgtaagc aatttagcgc tcgacaccca     180
gggagtaggc gactcctccc aggtagtggt cagcggctat gtattgccag gtctgcaagt     240
gaaatacggc gtgggtatat ttgactctat agcaacactc acgttacgtt atcgcctgat     300
gcctaagcta tatctggaag ccgtgtctgg tgtagaccag gcactggatt tgctctatca     360
gttcgagttt tagcaatgcg aatatttgtc tacggcagtt tacgccacaa acaaggcaac     420
agtcactgga tgaccaatgc ccagttactg ggcgatttca gtatcgataa ctaccagttg     480
tatagcctgg gccactatcc aggcgcagtt ccggggaacg gaacggtaca cggtgaagtt     540
tatcgtattg acaacgccac gctggccgaa cttgatgcct gcgcaccag gggcggtgaa     600 tacgcgcgcc agttgattca gacgccgtac gggagtgcat ggatgtacgt ttatcaacga     660
cccgtcgatg gattaaagct aattgaaagc ggcgactggt tagacaggga taagtaacca     720
tatgcatacg ccaccttcgg gtggcgttgt tttttgcgag acgactcgca ttctgttttg     780
taattccctc acctttgct tttctctccg agccgctttc catatctatt aacgcataaa      840
aaactctgct ggcattcaca aatgcgcagg ggtaaaacgt ttcctgtagc accgtgagtt     900
atactttgta taacttaagg aggtgcagat gcgtattacc ataaaaagat gggggaacag     960
tgcaggtatg tcattcccag atatcgtaat gaaagaactt aacttacagc cggggcagag    1020
cgtggaggcg caagtgagca acaatcaact gattctgaca cccatctcca ggcgctactc    1080
```

```
gcttgatgaa ctgctggcac agtgtgacat gaacgccgcg gaacttagcg agcaggatgt    1140
ctggggtaaa tccacccctg cgggtgacga aatatggtaa agaaaagtga atttgaacgg    1200
ggagacattg tgctggttgg ctttgatcca gcaagcggcc atgaacag                 1248
```

<210> SEQ ID NO 6
<211> LENGTH: 911
<212> TYPE: DNA
<213> ORGANISM: Escherichia coli
<220> FEATURE:
<221> NAME/KEY: misc_feature
<222> LOCATION: (1)..(911)
<223> OTHER INFORMATION: Deletion-carrying ytfP-yjfA region
<220> FEATURE:
<221> NAME/KEY: misc_feature
<222> LOCATION: (1)..(383)
<223> OTHER INFORMATION: 5' flank of the ytfP-yjfA region
<220> FEATURE:
<221> NAME/KEY: misc_feature
<222> LOCATION: (384)..(911)
<223> OTHER INFORMATION: 3' flank of the ytfP-yjfA region
<220> FEATURE:
<221> NAME/KEY: misc_feature
<222> LOCATION: (376)..(378)
<223> OTHER INFORMATION: ATG codon of the truncated ORF ytfP
<220> FEATURE:
<221> NAME/KEY: misc_feature
<222> LOCATION: (388)..(390)
<223> OTHER INFORMATION: ATG codon of the truncated ORF yjfA

<400> SEQUENCE: 6

```
ggcgatgtcg caacaagctg ccttgtctta tttgctacgt ggacaagggc tggagagcga      60
tcagagcgac agtgcggcaa tgacctcgat gctgattggt ttgggggttg cgcaaagtgg     120
ccagattgtg ggtaaaatcg gcgagacgtt tggcgtaagc aatttagcgc tcgacaccca     180
gggagtaggc gactcctccc aggtagtggt cagcggctat gtattgccag gtctgcaagt     240
gaaatacggc gtgggtatat ttgactctat agcaacactc acgttacgtt atcgcctgat     300
gcctaagcta tatctggaag ccgtgtctgg tgtagaccag gcactggatt tgctctatca     360
gttcgagttt tagcaatgcg aattatgcat acgccacctt cgggtggcgt tgttttttgc     420
gagacgactc gcattctgtt ttgtaattcc ctcacctttt gcttttctct ccgagccgct     480
ttccatatct attaacgcat aaaaaactct gctggcattc acaaatgcgc aggggtaaaa     540
cgtttcctgt agcaccgtga gttatacttt gtataactta aggaggtgca gatgcgtatt     600
accataaaaa gatgggggaa cagtgcaggt atggtcattc caatatcgt aatgaaagaa      660 cttaacttac agccggggca gagcgtggag gcgcaagtga gcaacaatca actgattctg     720
acacccatct ccaggcgcta ctcgcttgat gaactgctgg cacagtgtga catgaacgcc     780
gcggaactta gcgagcagga tgtctggggt aaatccaccc ctgcgggtga cgaaatatgg     840
taaagaaaag tgaatttgaa cggggagaca ttgtgctggt tggctttgat ccagcaagcg     900
gccatgaaca g                                                         911
```

<210> SEQ ID NO 7
<211> LENGTH: 1158
<212> TYPE: DNA
<213> ORGANISM: Escherichia coli
<220> FEATURE:
<221> NAME/KEY: misc_feature
<222> LOCATION: (1)..(1158)
<223> OTHER INFORMATION: Deletion-carrying ytfP-yjfA region
<220> FEATURE:
<221> NAME/KEY: misc_feature
<222> LOCATION: (1)..(630)
<223> OTHER INFORMATION: 5' flank of the ytfP-yjfA region

```
<220> FEATURE:
<221> NAME/KEY: misc_feature
<222> LOCATION: (631)..(1158)
<223> OTHER INFORMATION: 3' flank of the ytfP-yjfA region
<220> FEATURE:
<221> NAME/KEY: misc_feature
<222> LOCATION: (376)..(378)
<223> OTHER INFORMATION: ATG codon of the truncated ORF ytfP
<220> FEATURE:
<221> NAME/KEY: misc_feature
<222> LOCATION: (635)..(637)
<223> OTHER INFORMATION: ATG codon of the truncated ORF yjfA

<400> SEQUENCE: 7
ggcgatgtcg caacaagctg ccttgtctta tttgctacgt ggacaagggc tggagagcga      60
tcagagcgac agtgcggcaa tgacctcgat gctgattggt ttgggggttg cgcaaagtgg     120
ccagattgtg ggtaaaatcg gcgagacgtt tggcgtaagc aatttagcgc tcgacaccca     180
gggagtaggc gactcctccc aggtagtggt cagcggctat gtattgccag gtctgcaagt     240
gaaatacggc gtgggtatat tgactctat agcaacactc acgttacgtt atcgcctgat     300
gcctaagcta tatctggaag ccgtgtctgg tgtagaccag gcactggatt tgctctatca     360
gttcgagttt tagcaatgcg aatatttgtc tacggcagtt tacgccacaa acaaggcaac     420
agtcactgga tgaccaatgc ccagttactg ggcgatttca gtatcgataa ctaccagttg     480
tatagcctgg ccactatcc aggcgcagtt ccggggaacg gaacggtaca cggtgaagtt     540
tatcgtattg acaacgccac gctggccgaa cttgatgcct tgcgcaccag gggcggtgaa     600
tacgcgcgcc agttgattca gacgccgtac tatgcatacg ccaccttcgg gtggcgttgt     660
tttttgcgag acgactcgca ttctgttttg taattccctc accttttgct tttctctccg     720
agccgctttc catatctatt aacgcataaa aaactctgct ggcattcaca aatgcgcagg     780
ggtaaaacgt ttcctgtagc accgtgagtt atactttgta taacttaagg aggtgcagat     840
gcgtattacc ataaaaagat gggggaacag tgcaggtatg gtcattccca atatcgtaat     900
gaaagaactt aacttacagc cggggcagag cgtggaggcg caagtgagca acaatcaact     960
gattctgaca cccatctcca ggcgctactc gcttgatgaa ctgctggcac agtgtgacat    1020
gaacgccgcg gaacttagcg agcaggatgt ctggggtaaa tccacccctg cgggtgacga    1080
aatatggtaa agaaaagtga atttgaacgg ggagacattg tgctggttgg ctttgatcca    1140
gcaagcggcc atgaacag                                                  1158

<210> SEQ ID NO 8
<211> LENGTH: 20
<212> TYPE: DNA
<213> ORGANISM: Artificial Sequence
<220> FEATURE:
<223> OTHER INFORMATION: Description of the Artificial Sequence: Primer
      pckA'5'-1

<400> SEQUENCE: 8
gatccgagcc tgacaggtta                                                  20

<210> SEQ ID NO 9
<211> LENGTH: 20
<212> TYPE: DNA
<213> ORGANISM: Artificial Sequence
<220> FEATURE:
<223> OTHER INFORMATION: Description of the Artificial Sequence: Primer
      pckA'5'-2
```

```
<400> SEQUENCE: 9
gcatgcgctc ggtcaggtta                                                      20

<210> SEQ ID NO 10
<211> LENGTH: 22
<212> TYPE: DNA
<213> ORGANISM: Artificial Sequence
<220> FEATURE:
<223> OTHER INFORMATION: Description of the Artificial Sequence: Primer
      pckA'3'-1

<400> SEQUENCE: 10
aggcctgaag atggcactat cg                                                   22

<210> SEQ ID NO 11
<211> LENGTH: 20
<212> TYPE: DNA
<213> ORGANISM: Artificial Sequence
<220> FEATURE:
<223> OTHER INFORMATION: Description of the Artificial Sequence: Primer
      pckA'3'-2

<400> SEQUENCE: 11
ccggagaagc gtaggtgtta                                                      20

<210> SEQ ID NO 12
<211> LENGTH: 20
<212> TYPE: DNA
<213> ORGANISM: Artificial Sequence
<220> FEATURE:
<223> OTHER INFORMATION: Description of the Artificial Sequence: Primer
      Gdh1

<400> SEQUENCE: 12
tgaacacttc tggcggtacg                                                      20

<210> SEQ ID NO 13
<211> LENGTH: 20
<212> TYPE: DNA
<213> ORGANISM: Artificial Sequence
<220> FEATURE:
<223> OTHER INFORMATION: Description of the Artificial Sequence: Primer
      Gdh2

<400> SEQUENCE: 13
cctcggcgaa gctaatatgg                                                      20

<210> SEQ ID NO 14
<211> LENGTH: 20
<212> TYPE: DNA
<213> ORGANISM: Artificial Sequence
<220> FEATURE:
<223> OTHER INFORMATION: Description of the Artificial Sequence: Primer
      RhtC1

<400> SEQUENCE: 14
ctgttagcat cggcgaggca                                                      20

<210> SEQ ID NO 15
<211> LENGTH: 20
<212> TYPE: DNA
<213> ORGANISM: Artificial Sequence
<220> FEATURE:
<223> OTHER INFORMATION: Description of the Artificial Sequence: Primer
      RhtC2
```

-continued

```
<400> SEQUENCE: 15
gcatgttgat ggcgatgacg                                                 20

<210> SEQ ID NO 16
<211> LENGTH: 20
<212> TYPE: DNA
<213> ORGANISM: Artificial Sequence
<220> FEATURE:
<223> OTHER INFORMATION: Description of the Artificial Sequence: Primer
      Tdh1

<400> SEQUENCE: 16
tcgcgaccta taagtttggg                                                 20

<210> SEQ ID NO 17
<211> LENGTH: 20
<212> TYPE: DNA
<213> ORGANISM: Artificial Sequence
<220> FEATURE:
<223> OTHER INFORMATION: Description of the Artificial Sequence: Primer
      Tdh2

<400> SEQUENCE: 17
aataccagcc cttgttcgtg                                                 20

<210> SEQ ID NO 18
<211> LENGTH: 20
<212> TYPE: DNA
<213> ORGANISM: Artificial Sequence
<220> FEATURE:
<223> OTHER INFORMATION: Description of the Artificial Sequence: Primer
      ytfP-1

<400> SEQUENCE: 18
ggcgatgtcg caacaagctg                                                 20

<210> SEQ ID NO 19
<211> LENGTH: 20
<212> TYPE: DNA
<213> ORGANISM: Artificial Sequence
<220> FEATURE:
<223> OTHER INFORMATION: Description of the Artificial Sequence: Primer
      ytfP-2

<400> SEQUENCE: 19
ctgttcatgg ccgcttgctg                                                 20
```